US012635952B2

(12) United States Patent
Downey

(10) Patent No.: US 12,635,952 B2
(45) Date of Patent: May 26, 2026

(54) REMOVING LATENT NOISE COMPONENTS FROM DATA SIGNALS

(71) Applicant: University of Florida Research Foundation, Inc., Gainesville, FL (US)

(72) Inventor: Ryan James Downey, Gainesville, FL (US)

(73) Assignee: UNIVERSITY OF FLORIDA RESEARCH FOUNDATION, Inc., Gainesville, FL (US)

( * ) Notice: Subject to any disclaimer, the term of this patent is extended or adjusted under 35 U.S.C. 154(b) by 535 days.

(21) Appl. No.: 18/245,496

(22) PCT Filed: Aug. 25, 2021

(86) PCT No.: PCT/US2021/071283

§ 371 (c)(1),
(2) Date: Mar. 15, 2023

(87) PCT Pub. No.: WO2022/061322

PCT Pub. Date: Mar. 24, 2022

(65) Prior Publication Data

US 2023/0363718 A1     Nov. 16, 2023

Related U.S. Application Data

(60) Provisional application No. 63/080,475, filed on Sep. 18, 2020.

(51) Int. Cl.
*A61B 5/00*          (2006.01)
*A61B 5/291*        (2021.01)
          (Continued)

(52) U.S. Cl.
CPC ............ *A61B 5/7203* (2013.01); *A61B 5/291* (2021.01); *A61B 5/31* (2021.01); *A61B 5/369* (2021.01); *A61B 5/389* (2021.01); *A61B 5/398* (2021.01)

(58) Field of Classification Search
None
See application file for complete search history.

(56) References Cited

U.S. PATENT DOCUMENTS

2013/0072809 A1*  3/2013  Wilson ..................... A61B 5/30
                                                              600/544
2014/0203797 A1    7/2014  Stivoric et al.
                              (Continued)

FOREIGN PATENT DOCUMENTS

WO          2020146864 A1    7/2020

OTHER PUBLICATIONS

International Search Report and Written Opinion mailed on Dec. 14, 2021 for PCT Patent Application PCT/US2021/071283.

*Primary Examiner* — Aurelie H Tu
(74) *Attorney, Agent, or Firm* — Thomas I Horstemeyer, LLP

(57)          ABSTRACT

The present disclosure provides systems and methods for removing artifacts from data signals. One such method comprises obtaining a data signal across a plurality of data channels, wherein the data signal has artifacts across one or more channels; obtaining a reference signal representing noise activity across a plurality of noise channels; analyzing the data signal with the reference signal to identify noise components that exist within both the data signal and the reference signal; scaling the noise components to project upon the data signal across the plurality of channels; and/or cleaning the data signal by subtracting the scaled noise components from the data signal across individual ones of the data channels. Other methods and systems are also provided.

20 Claims, 30 Drawing Sheets

Typical EEG Electrode

Dual-Layer Noise Electrode

EOG Electrode

EMG Electrodes

(51) Int. Cl.

| | |
|---|---|
| *A61B 5/31* | (2021.01) |
| *A61B 5/369* | (2021.01) |
| *A61B 5/389* | (2021.01) |
| *A61B 5/398* | (2021.01) |

(56) References Cited

U.S. PATENT DOCUMENTS

| | | |
|---|---|---|
| 2015/0088024 A1 | 3/2015 | Sackellares et al. |
| 2018/0239430 A1 | 8/2018 | Tadi et al. |
| 2020/0077902 A1 | 3/2020 | Angle et al. |
| 2022/0071538 A1* | 3/2022 | Russomanno ......... A61B 5/297 |

\* cited by examiner

Noise
Electrode

Cortical / EEG
Electrode

Typical
EEG
Electrode

Dual-Layer
Noise
Electrode

EOG
Electrode

EMG
Electrodes

Recorded while stationary with only brain active. Mostly looks good but there is some line noise Vertical line represents when the "brain" inside the head phantom was turned on Line noise is removed obviously from this channel but also from all channels.

Importantly, no accidentally deletion of brain signals.

Line noise is
removed from
all channels.

No brain activity
removed by
mistake

Hexapod moved
to mimic walking.

High amplitude
motion artifact in
multiple channels.

Vertical line
represents when
the "brain"
inside the head
phantom was
turned on

Hexapod moved
to mimic walking.

High amplitude
motion artifact
deleted.

Vertical line
represents when
the "brain"
inside the head
phantom was
turned on

Note: it took only
10 seconds to
process 300
seconds worth of
data.

Motion artifact
that was deleted

Hexapod
stationary

Four neck muscles
contaminate many
EEG channels.

Vertical line
represents when
the "brain" and
"neck muscles"
inside the head
phantom were
turned on Hexapod stationary All muscle artifacts removed Vertical line represents when the "brain" inside the head phantom was turned on Muscle artifacts
that were
deleted Clean EEG Raw Noise Raw EEG Projected Noise Components

REMOVING LATENT NOISE COMPONENTS FROM DATA SIGNALS

CROSS-REFERENCE TO RELATED APPLICATIONS

This application is the 35 U.S.C. § 371 national stage application of International Application No. PCT/US2021/071283, filed Aug. 25, 2021, which claims priority to U.S. provisional application entitled, "A Novel Electroencephalography (EEG) Cleaning Algorithm that Uses Reference Noise Recordings and Canonical Correlation Analysis to Identify and Remove Artifacts," having Ser. No. 63/080,475, filed Sep. 18, 2020, which is entirely incorporated herein by reference.

STATEMENT REGARDING FEDERALLY SPONSORED RESEARCH OR DEVELOPMENT

This invention was made with Government support under U01 AG061389 awarded by the National Institutes of Health. The Government has certain rights in this invention.

This invention was made with Government support under W911NF-10-2-0022 awarded by The United States Army Research Development Engineering Command under a subcontract received from DCS Corporation.

TECHNICAL FIELD

The present disclosure is generally related to techniques for removing artifacts from data signals.

BACKGROUND

Electroencephalography (EEG) is very susceptible to artifacts because the signals it attempts to measure on the scalp are so small (tens of microvolts, uV). Although improvements to the EEG hardware (actively amplified electrodes) have helped provide cleaner raw EEG signals, motion-related artifacts are still a major obstacle to recording/analyzing brain activity during whole body movement. This limits both scientific research as well as commercial applications (e.g., brain computer interfaces for exoskeletons, virtual reality, and neuro-rehabilitation).

SUMMARY

Embodiments of the present disclosure provide a systems and methods for removing artifacts from data signals. Briefly described, one embodiment of the method, among others, comprises obtaining, by at least one computing device, a data signal across a plurality of data channels, wherein the data signal has artifacts across one or more channels; obtaining, by the at least one computing device, a reference signal representing noise activity across a plurality of noise channels; analyzing, by the at least one computing device, the data signal with the reference signal to identify noise components that exist within both the data signal and the reference signal; scaling, by the at least one computing device, the noise components to project upon the data signal across the plurality of channels; and/or cleaning, by the at least one computing device, the data signal by subtracting the scaled noise components from the data signal across individual ones of the data channels.

The present disclosure can also be viewed as providing systems for removing artifacts from data signals, such as, but not limited to, electroencephalography (EEG) data signals. One such system includes a plurality of electroencephalography (EEG) electrodes positioned facing towards a head of a subject, wherein the plurality of EEG electrodes are configured to record a data signal representing brain activity of the subject across a plurality of EEG channels. The system further includes a plurality of noise electrodes positioned facing away from the head of the subject wherein the plurality of noise electrodes are configured to record a reference signal representing noise activity across a plurality of noise channels; and a computing device. The computing device stores a signal cleaning program including computer-executable instructions configured to perform operations comprising: obtaining a recorded data signal representing the brain activity across the plurality of EEG channels, wherein the recorded data signal has artifacts across one or more EEG channels; obtaining a recorded reference signal representing the noise activity across the plurality of noise channels; analyzing the recorded data signal with the recorded reference signal to identify noise components that exist within both the recorded data signal and the recorded reference signal; scaling the noise components to project upon the recorded data signal across the plurality of EEG channels; and/or cleaning the recorded data signal by subtracting the scaled noise components from the recorded data signal across individual ones of the EEG channels.

In one or more aspects for such systems/methods, the noise components are identified using Canonical Correlation Analysis (CCA); the data signal represents brain activity across a plurality of electroencephalography (EEG) channels, wherein the plurality of data channels comprise the plurality of electroencephalography (EEG) channels; the plurality of noise electrodes comprise electromyogram (EMG) sensors; the plurality of noise electrodes comprise electrooculogram (EOG) sensors; individual ones of the plurality of EEG electrodes and individual ones of the plurality of noise electrodes are integrated in a dual-layer sensor; the artifacts comprise motion artifacts; the artifacts comprise line noise; the artifacts comprise muscle artifacts; and/or the artifacts comprise eye artifacts.

In one or more aspects for such systems/methods, an exemplary system/method can further perform operations comprising positioning a plurality of EEG electrodes facing towards a head of a subject, wherein the plurality of EEG electrodes record the data signal across the plurality of EEG channels; positioning a plurality of noise electrodes facing away from the head of the subject wherein the plurality of noise electrodes record the reference signal across the plurality of noise channels; positioning a plurality of dual-layer sensors on a head of a subject, wherein an individual dual-layer sensor has an EEG electrode facing towards the head of the subject and a noise electrode facing away from the head of the subject, wherein a plurality of EEG electrodes record the data signal across the plurality of EEG channels and a plurality of noise electrodes record the reference signal across the plurality of noise channels; determining an optimal scaling factor that explains how each noise component projects onto each of the plurality of data channels, wherein the noise components are scaled using the optimal scaling factor; and/or wherein after cleaning the data signal, noise sources that overlap with a data of interest are deleted without deleting the data of interest.

Other systems, methods, features, and advantages of the present disclosure will be or become apparent to one with skill in the art upon examination of the following drawings and detailed description. It is intended that all such additional systems, methods, features, and advantages be included within this description and be within the scope of the present disclosure.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

The present disclosure describes various embodiments of systems, apparatuses, and methods for removing artifacts from data signals, such as electroencephalography (EEG) data signals. As discussed, motion-related artifacts are a major obstacle to recording/analyzing brain activity during whole body movement. This limits both basic research as well as commercial applications (e.g., brain computer interfaces, neuro-rehabilitation, etc.).

Figure 1:
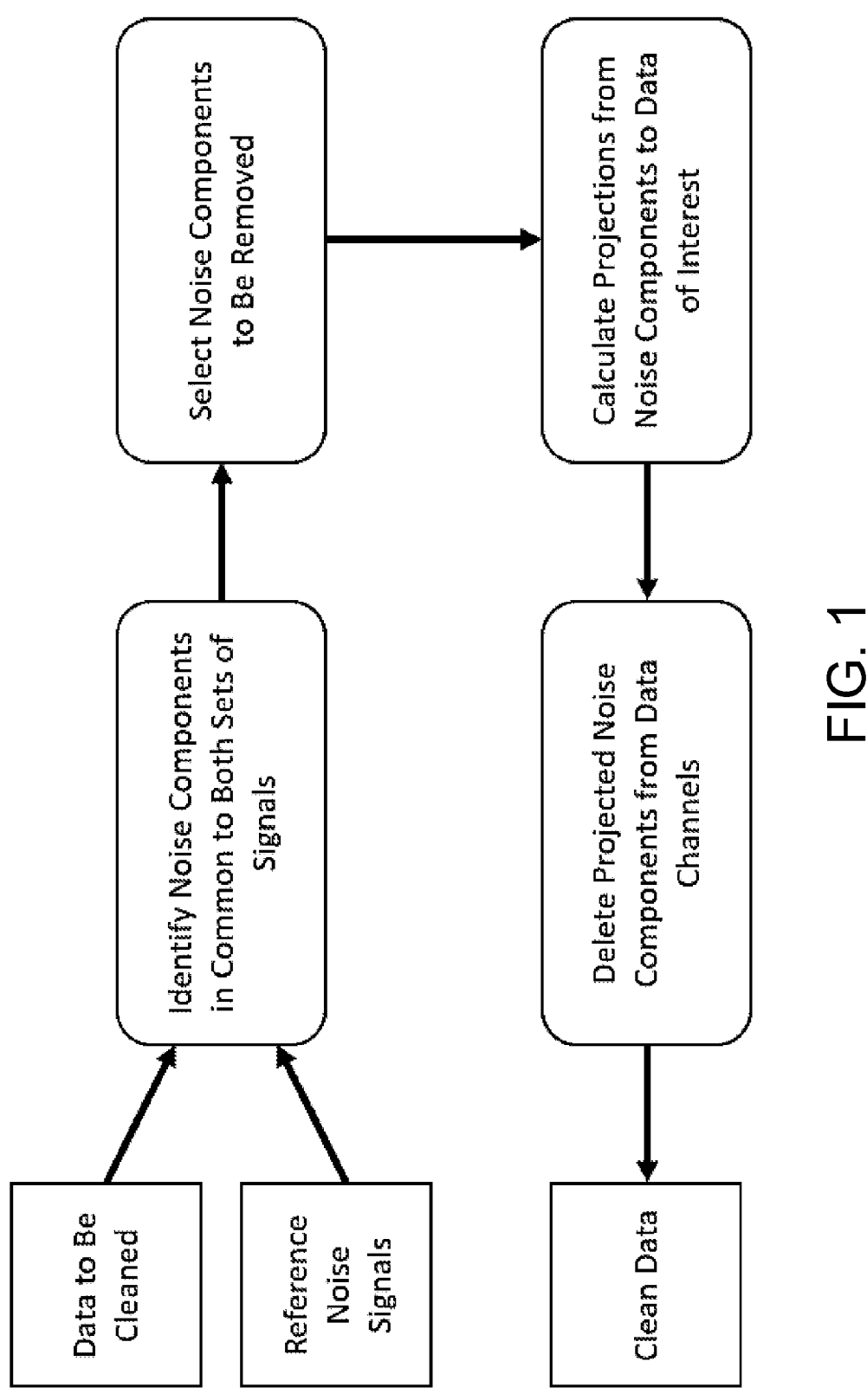
FIG. 1 outlines a general framework for an exemplary cleaning algorithm to take a set of noise signals and intelligently clean a set of signals of interest in accordance with embodiments of the present disclosure.

To overcome this limitation, novel systems and methods for cleaning EEG data have been developed. In accordance with embodiments of the present disclosure, an exemplary signal cleaning algorithm exploits direct recordings of artifacts (via noise sensors of various types) to find independent sources of noise that are significantly (statistically) contaminating EEG signals (or other signal of interest). The exemplary signal cleaning algorithm determines how these independent noise sources (components) project (scale) onto EEG channels (electrodes) and subtracts (deletes) the noise sources from the EEG channels. A basic visual outline of the approach is provided in FIG. 1. Results are subsequently shown for cleaning EEG signals but it is reasonably expected that other types of signals can be cleaned. Various embodiments are subsequently discussed.

Figure 2A:
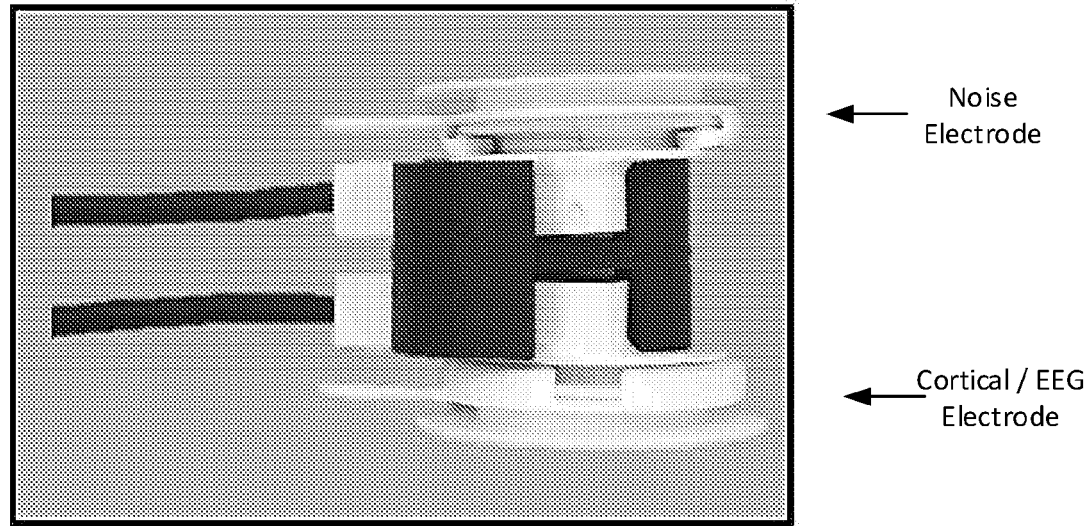
FIGS. 2A-2B show a photograph image of a prototype and a schematic diagram of an exemplary dual-layer electroencephalography (EEG) sensor having both a noise electrode and an EEG (or cortical) electrode in accordance with various embodiments of the present disclosure.
Figure 2B:
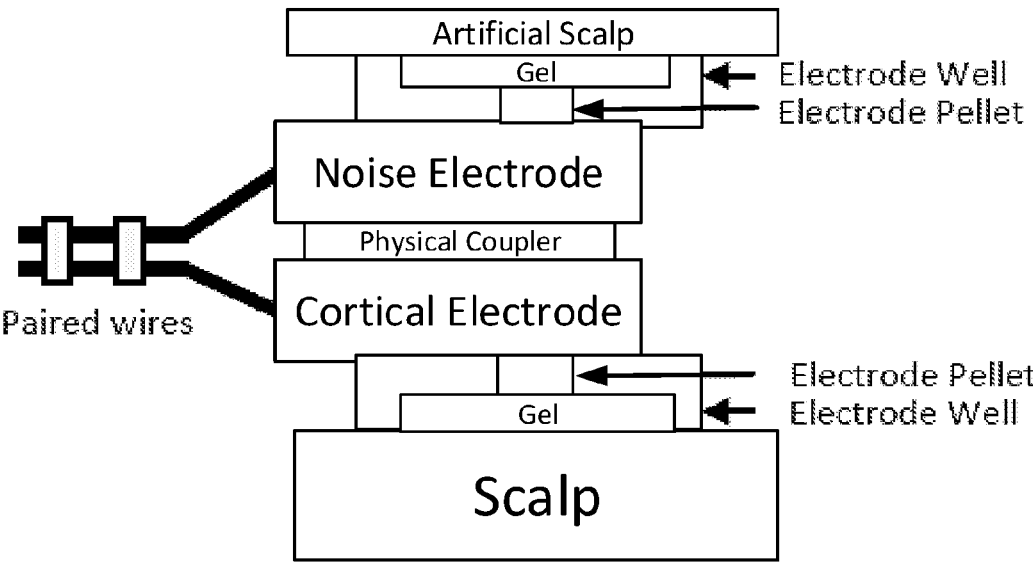
Figure 3:
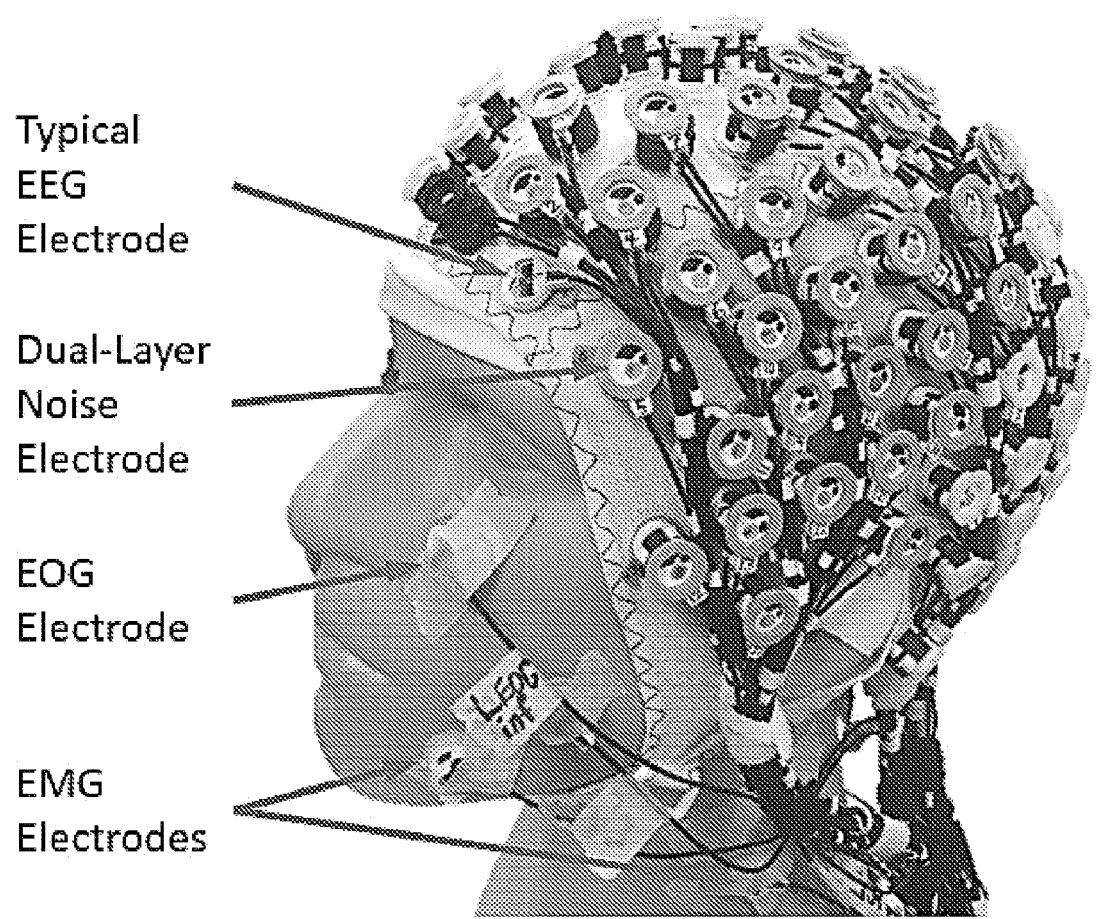
FIG. 3 shows a photograph image of a mannequin's head wearing a cap fitted with a plurality of dual-layer EEG sensors in accordance with various embodiments of the present disclosure.

In various embodiments, dual-layer EEG sensors are used to record raw noise signals (in addition to EEG signals). In accordance with various embodiments, FIGS. 2A-2B show a prototype image and a schematic diagram of an exemplary dual-layer EEG sensor having both a noise electrode and an EEG (or cortical) electrode. The dual-layer EEG sensors are configured so that EEG electrodes or sensors face the scalp of a subject and noise sensors are pointing away from the scalp. FIG. 3 shows a model of a mannequin's head wearing a cap fitted with a plurality of dual-layer EEG sensors as well as EMG and EOG sensors which can also be considered to be noise sensors but with the goal being to remove a different type of noise (e.g., to remove muscle artifacts and eye artifacts rather than motion artifacts and line noise). Note that conductive fabric is placed over the dual-layer EEG noise sensors (to serve as an artificial scalp/skin layer), but the conductive fabric is not present in FIG. 3 as it would obstruct the view of the sensors beneath. The EEG electrodes can record brain activity from the subject in addition to accidentally recording unwanted artifacts/noise from internal or external sources, while the noise electrodes attempt to record strictly noise signals (whether they be motion artifacts, line noise, eye artifacts, muscle artifacts, or other type of artifact). Thus, a noisy EEG signal from the EEG electrodes and a reference noise signal from the noise electrodes/sensors have in common the noise from internal or external sources. It is noted that additional electrodes (besides the dual-layer EEG sensors) are present on the mannequin, specifically, below the eye (electrooculogram sensors, EOG) and over the jaw and neck muscles (electromyogram sensors, EMG). Techniques of the present disclosure can remove a variety of artifacts that commonly contaminate EEG signals so long as the appropriate noise recording(s) is/are available (e.g., dual-layer sensor for motion artifact and line noise removal, EMG for removing contamination by muscle contractions, EOG for eye blink and saccade removal, etc.). Each of these three aforementioned types of noise sensors has been tested/validated and results are shown in the present disclosure. Note, however, it is expected that the techniques of the present disclosure are capable of removing other artifacts given reference signals from other types of noise sensors. For example, it is likely that heartbeat and pulse artifacts can be removed from EEG signals using electrocardiogram (ECG/EKG) signals. Similarly, it is expected that magnetic resonance imaging (MRI) artifacts could be removed from EEG signals by recording raw noise signals coming from the MRI scanner. Along these lines, while the results in the present disclosure focus on the cleaning of EEG signals, it is conceivable that the techniques of the present disclosure can be implemented with little-to-no modification for the cleaning of other types of signals.

For example, EMG signals could be cleaned using their own version of a dual-layer sensor to record and later delete motion artifacts.

In accordance with various embodiments of the present disclosure, an exemplary cleaning algorithm uses Canonical Correlation Analysis (CCA) to identify latent relationships between the noise electrodes and the EEG electrodes and thereby find the noise components that are contaminating the EEG signals so that the noise components can subsequently be removed. In various embodiments, CCA can provide the noise components in a ranked order according to their correlation strength so that components above a certain threshold value can be marked for removal. In various embodiments, an exemplary computing system may be configured with a knob or other controller to select or adjust the threshold value as desired, although note there are other options for selecting a subset of CCA components for removal as will be subsequently discussed. Once a subset of components has been identified for removal with the exemplary cleaning algorithm, the noise components are scaled and then subtracted from the raw EEG signals resulting in clean EEG signals.

Canonical Correlation Analysis (CCA) is a statistical method that is useful for inferring information between two sets of variables via their cross-covariance matrices. CCA finds relationships between two sets of variables X and Y, where X and Y can each be composed of many data channels (columns) and many samples (rows). For an input of raw data matrices (X, Y), CCA returns linear mixtures of X and Y which are labeled U and V, respectively, where U and V are sets of components (subspaces of X and Y) that are maximally correlated to each other. Note that the number of components returned from CCA (i.e., the number of columns in U and V) depend on the dimensions of X and Y such that it equals the minimum rank of X or Y, whichever is smaller. CCA also returns weight matrices A, B which define how the component sets U and V were extracted from the raw data ($U=X_{MC}A$, $V=Y_{MC}B$ where $X_{MC}$ and $Y_{MC}$ denote the mean centered versions of X and Y), along with a vector R which quantifies the correlation between U and V. In ranking the results, $U_1$ is the mixture (or subspace) of X that is most correlated with a mixture (or subspace) of Y ($V_1$), $U_2$ is the next mixture of X that is most strongly correlated with a mixture of Y ($V_2$), and so on with every UV pair being independent from the others. In accordance with various embodiments of the present disclosure, CCA is used to find latent relationships between signals recorded via noise electrodes and signals recorded via EEG electrodes. In doing so, CCA returns mixtures of the EEG channels (i.e., components or subspaces) that most strongly resemble mixtures of the noise channels. Since the resulting components are returned in ranked order, a subset of noise components can be easily identified by using a simple threshold (e.g., by marking all components with an R-squared value greater than some desired cutoff value as being components that should be removed). However, other approaches could be employed for selecting a subset of CCA components for removal such as examining the power spectra of the components (e.g., to verify a particular component's power spectral profile resembles that of noise rather than brain activity) or by using a random resampling (e.g., bootstrapping) approach to determine correlation values that occur above chance level rather than a priori picking a particular value for a threshold. Importantly, note that the noise channels need not be the noise sensors of the dual-layer system depicted in FIGS. 2A-2B and 3; the noise channels can also be electromyography (EMG) sensors placed over muscles whose activity contaminates EEG signals or similarly sensors capturing eye artifacts (electrooculogram; EOG), or any other type of sensor capable of recording artifacts the user wishes to remove.

Once a subset of noise components has been identified, their presence on the EEG channels (or other signals of interest) may be removed. Since the amplitudes of the noise components (U, V) returned by CCA are normalized by default and since the amount of noise present on each EEG channel varies, the noise components must first be appropriately scaled to each EEG channel prior to deletion. Thus, to remove the noise components, an exemplary signal cleaning algorithm determines an optimal scaling factor that explains how each component (or a set of components) project(s) onto each noisy EEG channel (or other signal of interest) that is to be cleaned. This optimal scale factor can be determined in a number of ways, including for example by using the Moore-Penrose pseudoinverse to calculate the inverse mapping from noise components to channels, given the forward mapping from channels to components that CCA yielded (i.e., given weight matrices A, B such that $U=X_{MC}A$ and $V=Y_{MC}B$, use a pseudoinverse to solve for the inverse mapping). However, the inventor has found that using a more general least squares solution (without the additional minimum norm constraint of the pseudoinverse approach) outperformed a pseudoinverse when the number of noise channels is small compared to the number of EEG channels. Thus, in the figures of the present disclosure, an exemplary signal cleaning algorithm uses a least squares solution to solve for the noise projections such as is implemented by the MATLAB built-in functions for matrix division (mrdivide and mldivide). Once the optimal scaling factors have been calculated, the scaled (projected) version of the noise components is subtracted from each channel of the noisy EEG data. In various embodiments, U or V (or a mixture of the two) can be used as the noise components for subtraction as preferences dictate. In accordance with embodiments of the present disclosure, the exemplary signal cleaning algorithm makes use of all of the noise electrodes/sensors (multi-channel data, not looking at individual noise channel-EEG channel pairs) to calculate a set of independent, underlying noise sources/components. Then, the noise sources can be individually scaled and deleted (noise source by noise source and EEG channel by EEG channel). In this way, an exemplary algorithm, which utilizes CCA to first identify latent noise components, is better able to remove artifacts than approaches that simply scale up a single raw noise channel (not component) paired to a single raw EEG channel. Whereas in other approaches where a noise channel would have to perfectly capture the noise signal contaminating the EEG channel of interest, the present approach exploits the fact that multiple noise sensors and multiple EEG channels are available, each recording a slightly different version of multiple noise sources. This allows for the identification and separation of multiple sources of noise contaminating the EEG channels so these noise sources can be individually scaled appropriately to each channel before deletion.

Figure 4:
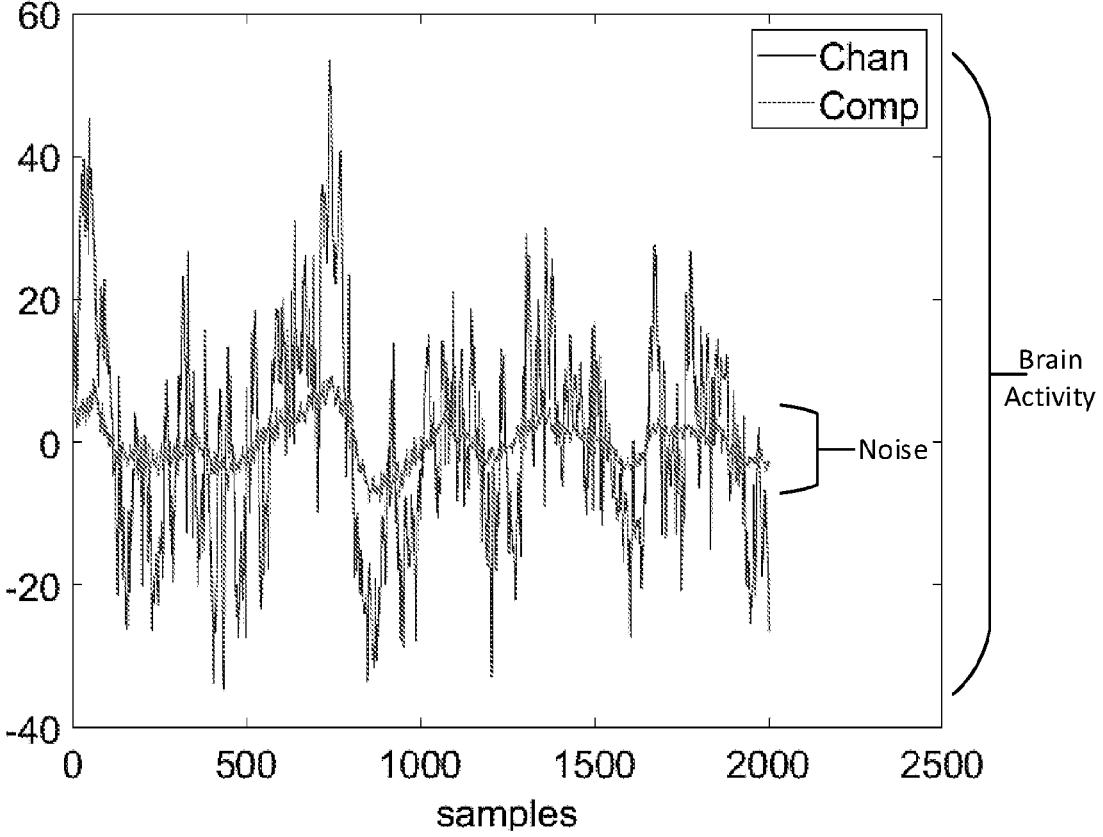
FIGS. 4-5 shows illustrative scaling of a noise component returned from Canonical Correlation Analysis (CCA) to find its projection onto a noisy EEG signal in accordance with various embodiments of the present disclosure.
Figure 5:
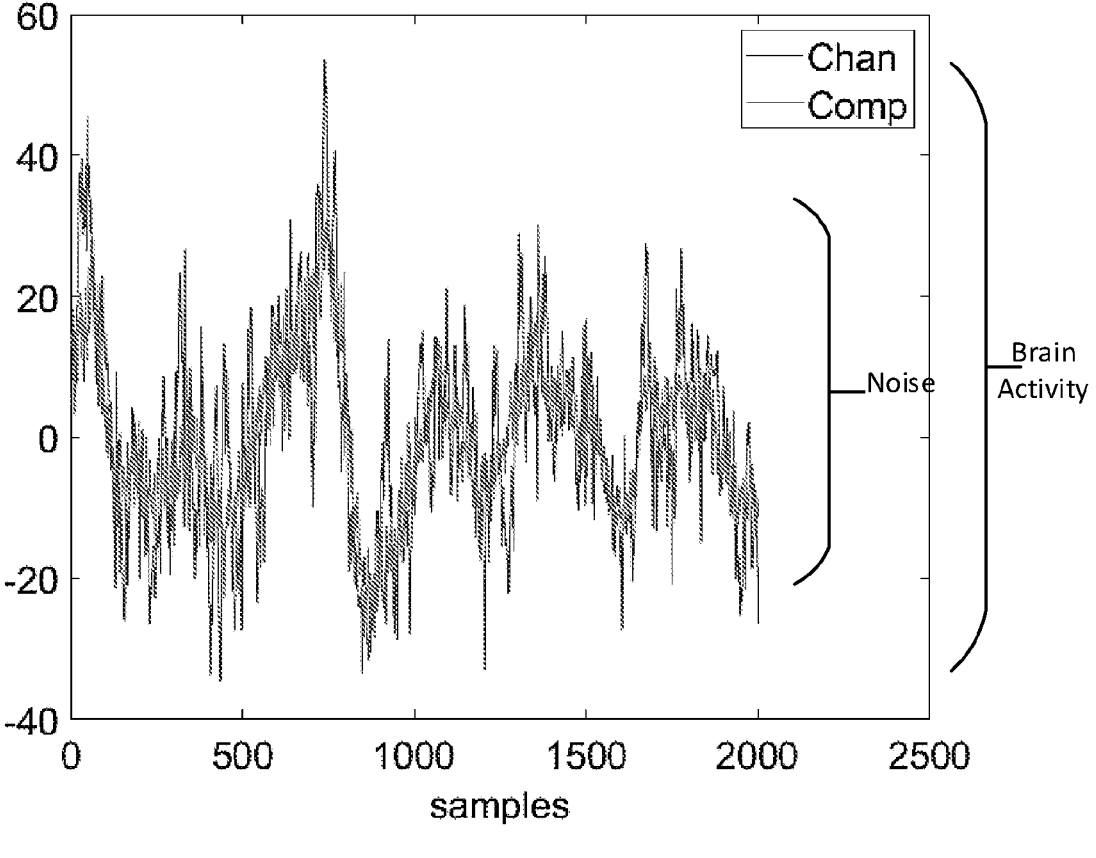
Figure 6:
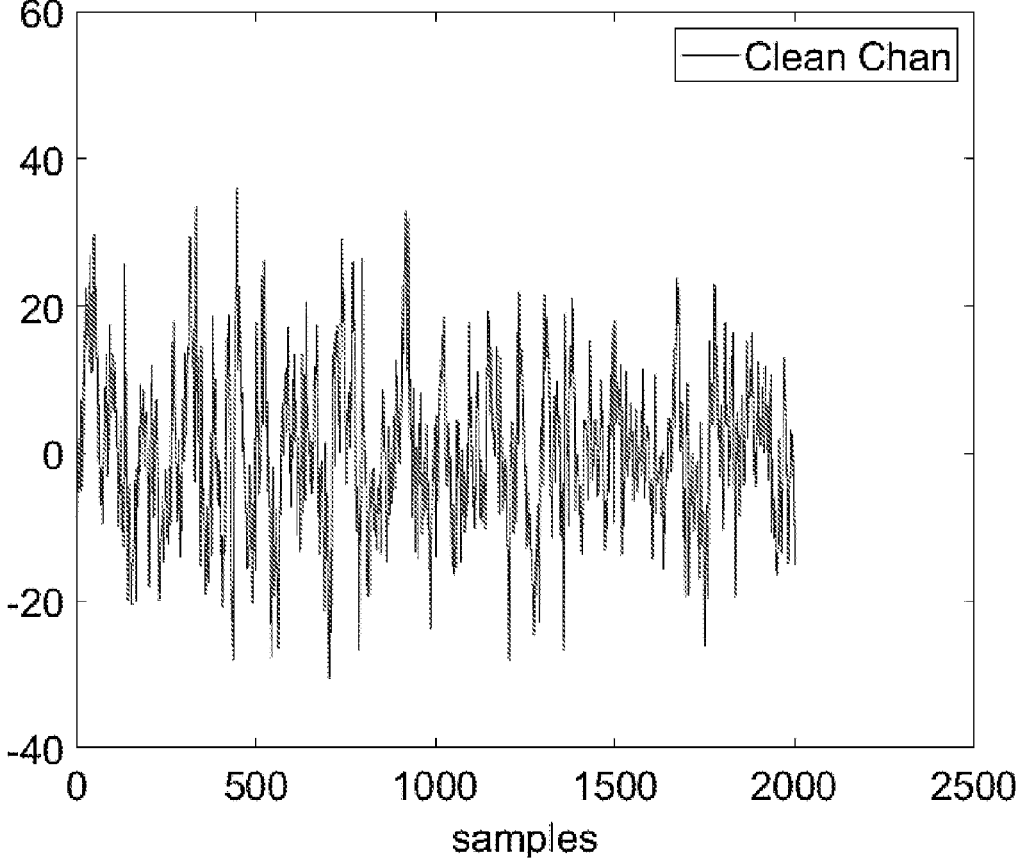
FIG. 6 shows a cleaned EEG signal after a scaled noise component has been removed in accordance with various embodiments of the present disclosure.

To illustrate the scaling operation, FIG. 4 shows improper scaling where an exemplary noise component is significantly smaller and out of scale in comparison to the noisy EEG signal it is contaminating. In comparison, FIG. 5 shows optimal scaling where the noise component selected for removal is scaled appropriately to the noisy EEG signal to be cleaned. Next, FIG. 6 shows the cleaned EEG signal after the scaled noise component has been removed, in accordance with embodiments of the present disclosure.

Exemplary systems and methods for removing artifacts from EEG signals using CCA analysis with reference noise recordings is novel and is an improvement over prior methods and systems. For instance, in 2017, Rasheed et al. developed a dual-electrode system to clean magnetic resonance imaging (MRI) artifacts from EEG signals. See Rasheed, Y-K. Lee, and S. Y. Lee, "Reference Layer Adaptive Filtering (RLAF) for EEG Artifact Reduction in Simultaneous EEG-fMRI Related Content Artifact Attenuation in EEG signals Acquired Inside MRI using Constrained ICA," 2017, doi: 10.1088/1741-2552/14/2/026003. First, the Rasheed approach tried directly subtracting the signal recorded by the noise sensor from that of the EEG sensor on a pair-by-pair basis, in which each EEG electrode had a corresponding noise sensor attached. This direct subtraction technique can only work if the noise sensor records all sources of noise exactly the same as they appear on the contaminated EEG sensor (same exact shape and magnitude) which, in practice, does not occur. Second, the Rasheed approach tried adaptively scaling the noise signals to better match the noisy EEG signals. While this approach can accommodate for differences in magnitude between the reference noise signal and the noisy EEG channel, the scaling still requires the noise sensor to record everything exactly the same as the EEG sensor besides a pure scaling factor. Unfortunately, in practice, this is not the case. For example, there could easily be two independent sources of noise that simultaneously project onto a single noise sensor-EEG sensor pair. It is nearly guaranteed that these two noise sources will project with a different ratio (one noise source relative to the other) onto the noise sensor than they project onto the EEG sensor. For example, suppose two noise sources project onto a noise sensor with amplitudes of 10 and 20 uV, respectively (a 1:2 ratio), while the same two noise sources project onto an EEG sensor with amplitudes of 10 and 40 uV, respectively (a 1:4 ratio). In this case, the two underlying sources of noise would need to be individually identified and scaled to remove them completely from the EEG channel of interest. The method by Rasheed et al. does not allow for this.

Meanwhile, an exemplary signal cleaning algorithm, in accordance with embodiments of the present disclosure, makes use of all of the noise sensors (multi-channel data, not simply considering individual noise-EEG pairs) to calculate a set of independent, underlying noise sources/components; and scale and delete the noise sources individually (noise source by noise source and EEG channel by EEG channel).

In 2018, Andrew Nordin et al. created a dual-electrode noise system for mobile EEG and tested a basic frequency domain-based algorithm for noise cleaning. See A. D. Nordin, W. D. Hairston, and D. P. Ferris, "Dual-Electrode Motion Artifact Cancellation for Mobile Electroencephalography," J. Neural Eng., vol. 15, no. 5, p. 056024, August 2018, doi: 10.1088/1741-2552/aad7d7. Specifically, the Nordin system took a fast Fourier Transform (FFT) of the EEG sensors as well as an FFT of the noise sensors. Then, the Nordin system set certain frequencies (those determined to have relatively large or small amplitudes on the FFT of the noise sensor data) in the EEG signal to have zero amplitude (to delete it). While this approach can work for simplified scenarios (e.g., when the motion artifact is a pure, constant sinusoid happening at a frequency that is completely independent from ongoing brain oscillations), it is not robust to artifacts from real world dynamic movement where motion artifacts are complex and changing. Along these lines, the Nordin approach has a strong potential to distort the signals it is supposed to clean. This stems from that fact that FFT is an approximation method. Specifically, just because a signal can be approximated by a summation of many sinusoids does not mean the signal was originally composed of sinusoids. If a noise source is not sinusoidal (but can be approximated by sinusoids) and some (but not all) of its sinusoidal components are deleted, then what is left over will be a distortion, and the situation has potentially been made worse than before. Further, if a motion artifact overlaps with brain signals in terms of its frequency content, then setting the EEG amplitude to zero at that 'motion artifact frequency' will cause all of the brain activity at that frequency to be deleted as well. In contrast, an exemplary signal cleaning algorithm, in accordance with embodiments of the present disclosure, is applied more intelligently such that noise sources that overlap in frequency content with data of interest, such as brain activity, are deleted without also accidentally deleting the brain activity itself. Accordingly, for other types of data signals, noise sources that overlap (e.g., overlap in frequency content, share characteristics, etc.) with the data of interest within the data signal(s) are deleted or removed without deleting the data of interest.

Independent component analysis (ICA) can also be used to help clean EEG signals. However, ICA is computationally expensive (on the order of hours to process data, often necessitating the use of supercomputer clusters to speed up the process). Further, one can run the same exact ICA algorithm twice in a row and obtain different results because it is a numerically driven minimization algorithm with random starting points. ICA also only considers the information from a single set of data channels (in this case, the EEG sensors and the noise sensors would have to be lumped together as one set of signals).

Diversely, an exemplary signal cleaning algorithm, in accordance with embodiments of the present disclosure, exploits the known relationship between the EEG sensors and the noise sensors (EEG sensors contain noise but noise sensors contain no brain activity), runs extremely fast (on the order of seconds to minutes for data that would otherwise take ICA hours), and will return the same results every time given the same input data and parameters. Specifically, an exemplary cleaning algorithm uses canonical correlation analysis (CCA) to identify independent subspaces within the noise sensors that are highly correlated with subspaces in the EEG recordings (i.e., the noisy subspaces within the EEG data). As discussed, a subset of identified noise components may then be scaled to find how they project onto the EEG sensors, such that the scaled version of the independent noise components may be removed from the EEG signal data in the time domain. It is noted that using ICA and using an exemplary CCA-based signal cleaning algorithm of the present disclosure need not be mutually exclusive. In fact, one useful application of the exemplary signal cleaning algorithm is to use it to remove problematic artifacts from raw EEG signals before later being passed on to ICA. ICA would then take the clean EEG channel data and decompose them into underlying brain sources. Thus, for real-time applications (where ICA would be too slow), users can apply the exemplary signal cleaning algorithm on its own; meanwhile, for offline applications, ICA can be used alongside the exemplary signal cleaning algorithm.

It is further noted that CCA has been in parts of cleaning algorithms in the past, but in different ways than the exemplary signal cleaning technique of the present disclosure. In these other approaches, CCA has been used alongside shifted or transformed versions of the original EEG signal. Thus, these approaches do not use noise sensors; instead, they create false (pseudo) signals for the second set of required inputs to CCA. For example, pseudo-EEG channels may be created from a 1-sample shifted (delayed) version of the original EEG and sent to CCA as the second set of input (Y), alongside the original EEG (X). This application of CCA may be referred to as 'auto-CCA' because, although CCA is used on multi-channel data (sets of signals), the sample shifted version of CCA is analogous to calculating the auto-correlation of one signal with itself, as opposed to calculating the cross-correlation between two independently recorded signals. In contrast, the exemplary systems and methods of the present disclosure uses CCA on two sets of signals which were separately recorded (the second input is not a simple manipulation of the first but rather a new, unique piece of information that can be exploited).

While the auto-CCA approach can work to delete artifacts (primarily muscle artifacts) the way it identifies noise sources and the theory behind the approach is lacking. Since the second set of signals is a one-sample delay of the original EEG, researchers have suggested that the low-frequency aspects of the EEG signal will naturally have high correlation and the high-frequency aspects of the EEG signal will have low correlation when CCA is used to examine correlations between the EEG signals and the pseudo-EEG signals. The general reasoning is that a one-sample shift barely changes the phase of very low frequency signals compared to higher frequency signals. Note, however, that there is a cross-over point where high frequencies begin to have high correlation again. Thus, technically speaking the situation is not as simple as the notion that low-frequencies will have high correlation with a 1-sample shift while high frequencies will have low correlation, as is presented in the literature. This is easily verified in simulation by creating sinusoidal signals at various frequencies, making a one-sample shifted copy of those signals, and then calculating the correlation between the original and the shifted version as a function of the underlying frequency. Nevertheless, the auto-CCA approach is premised on feeding a pseudo signal into CCA in attempt to split the EEG signals into various frequency bands where brain activity is expected to exist in different frequency bands than the noise the user wishes to be removed. Meanwhile, there is no guarantee that the frequency content of the artifacts and the underlying brain sources will be independent from each other.

Rather than using auto-CCA on one-sample shifted but otherwise raw multi-channel EEG data, others have attempted to use empirical mode decomposition (EMD) and ensemble empirical mode decomposition (EEMD) to transform each single channel of EEG data into a pseudo multi-channel set of signals prior to CCA (called EMD-CCA or EEMD-CCA). It is noted that EMD is a data-driven technique designed to split a single signal into high and low frequency components.

Thus, with both auto-CCA and EMD-CCA/EEMD-CCA, the EEG data are first split into high and low frequency components due to the assumption that the noise sources are going to exist predominantly in a particular frequency band that is separate from brain activity data and thus can be removed. Accordingly, these approaches do not find the true underlying noise sources since, generally speaking, there will be overlap in the frequency content of noise sources and brain sources, whereas exemplary systems and methods of the present disclosure find the underlying noise sources by applying CCA directly to the raw time series of the EEG electrodes and the noise electrodes (i.e. without a priori enforcing a constraint on the frequency content of the noise sources). It is also noted that EMD (and its extension ensemble empirical mode decomposition (EEMD)) take a long time to execute and are not useful for real-time applications.

Another point of distinction between the systems and methods of the present disclosure and previous CCA approaches is the manner in which artifacts are deleted. For example, with other CCA approaches it is often assumed a weight matrix will be calculated that takes noisy EEG channel data and decomposes it completely into (1) clean brain components and (2) noise/other components, because both of the inputs into CCA with these approaches are some form of EEG (i.e., brain) data (whether the pseudo-EEG data is first one-sample lagged or EMD transformed). The noise components are then set to zero and the weight matrix is used to project only the supposed brain components back onto the EEG channels, similar to the way that pruning works with independent component analysis (ICA). In contrast, actual noise sensors are used in the CCA of the exemplary cleaning algorithm, in accordance with embodiments of the present disclosure, rather than a pseudo set of signals (manipulated copy of the original EEG data). Since CCA finds how two sets of signals are dependent on each other (through some latent source that affects them both), the exemplary cleaning algorithm of the present disclosure identifies common components between the noisy EEG channels and the noise sensors (i.e., it should only find noise components since there is no brain activity in common). This is a different and novel approach to cleaning the EEG channels with CCA as compared to a traditional CCA approach, which follows the basic outline of an ICA pruning approach. After identifying the noise components (and only the noise components), the exemplary cleaning algorithm calculates how these noise components project onto the individual EEG channels and subtracts those noise projections from the original EEG channels. As such, exemplary systems and methods of the present disclosure operate by identifying and deleting noise projections (as opposed to calculating alleged brain projections and rejecting all but those alleged brain projections).

Figure 7:
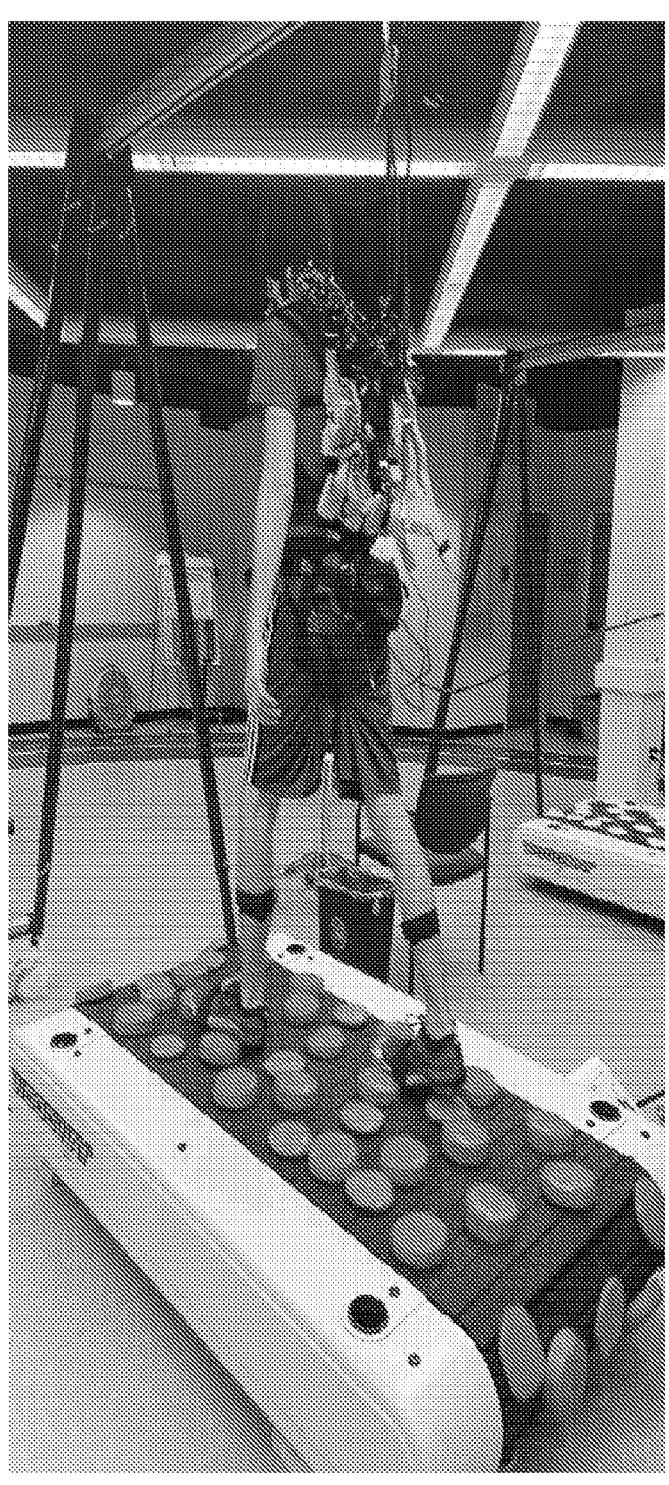
FIG. 7 shows a photograph image of a subject wearing noise electrodes and EEG electrodes as the subject walked over the uneven terrain of a treadmill in accordance with embodiments of the present disclosure.

For experimental analysis, an exemplary system was tested on human subjects while the subjects walked across a treadmill with uneven terrain (more likely to cause motion artifact than flat, level walking). Accordingly, FIG. 7 shows an image of a subject wearing noise electrodes and EEG electrodes as the subject walked over the uneven terrain of a treadmill. The noisy brain activity of the subject via the EEG electrodes and reference noise signals via the noise electrodes are recorded and processed using an exemplary signal cleaning algorithm, in accordance with embodiments of the present disclosure.

Figure 8A:
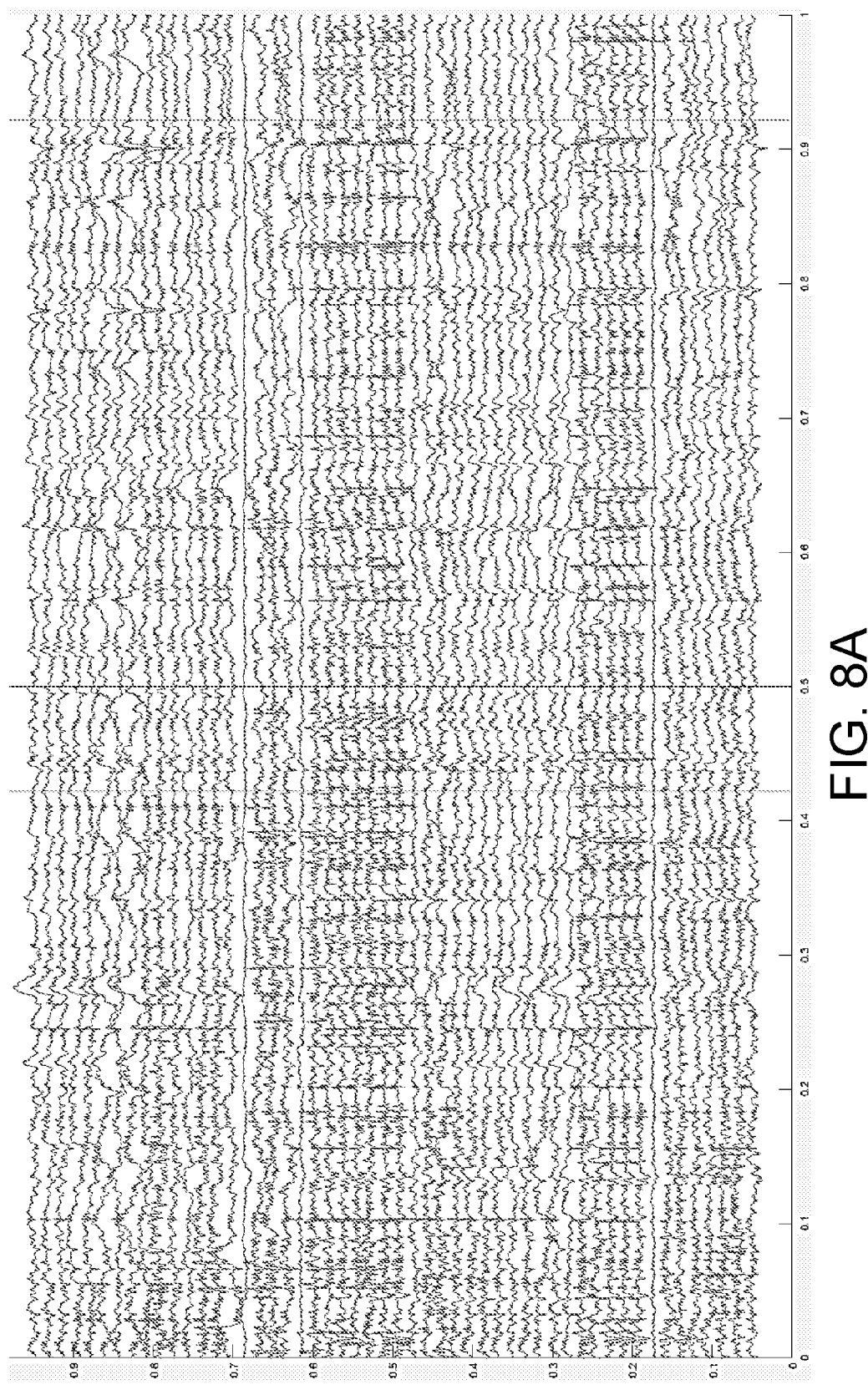
FIGS. 8A and 9A show raw EEG data recorded from the EEG electrodes/channels over two different 10-second-long segments with large motion artifacts (before cleaning) for a subject walking over a treadmill with uneven terrain.
Figure 8B:
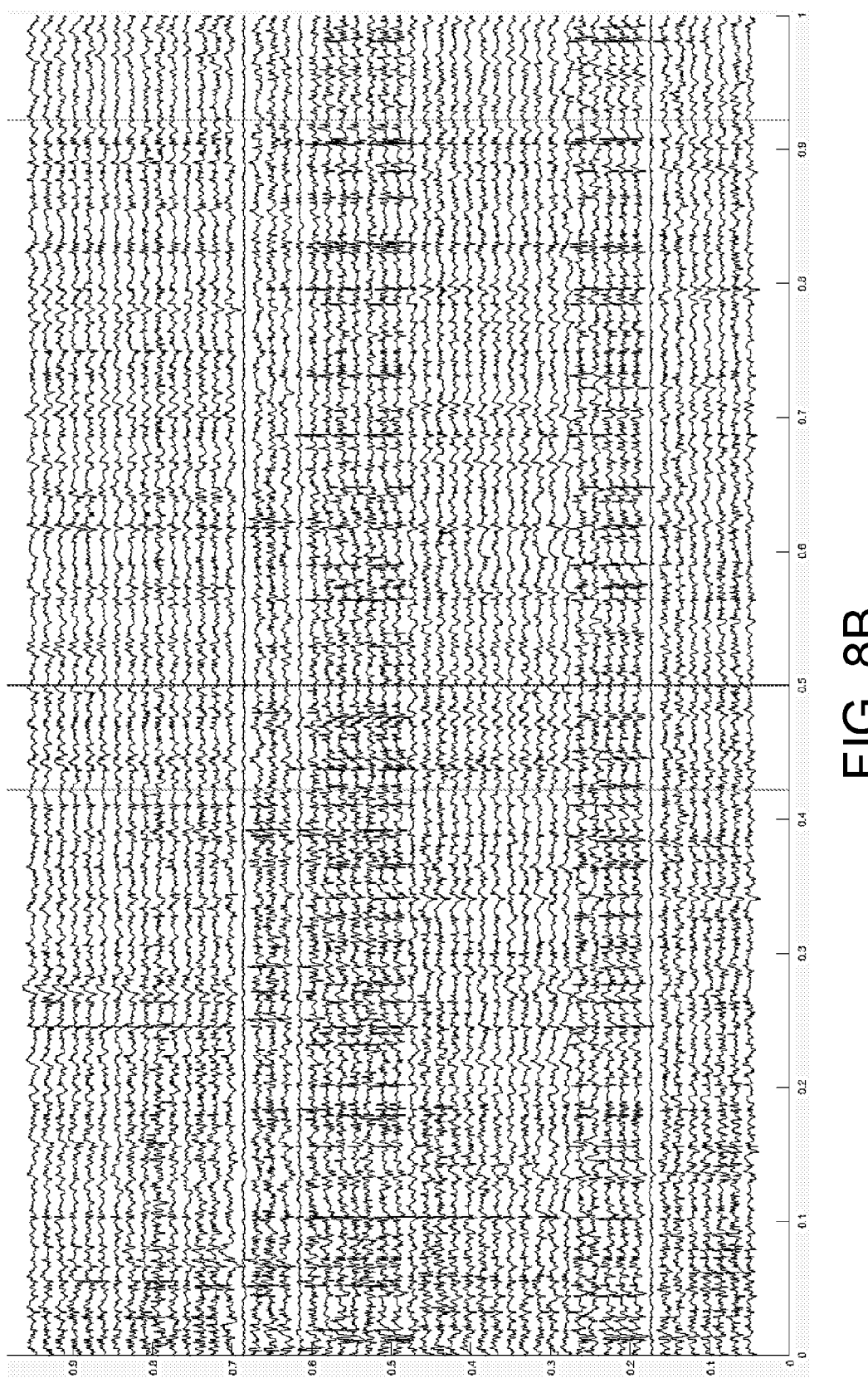
FIGS. 8B and 9B show the cleaned EEG data after the noise components have been removed using an exemplary system of the present disclosure for each of the respective 10-second segments.
Figure 8C:
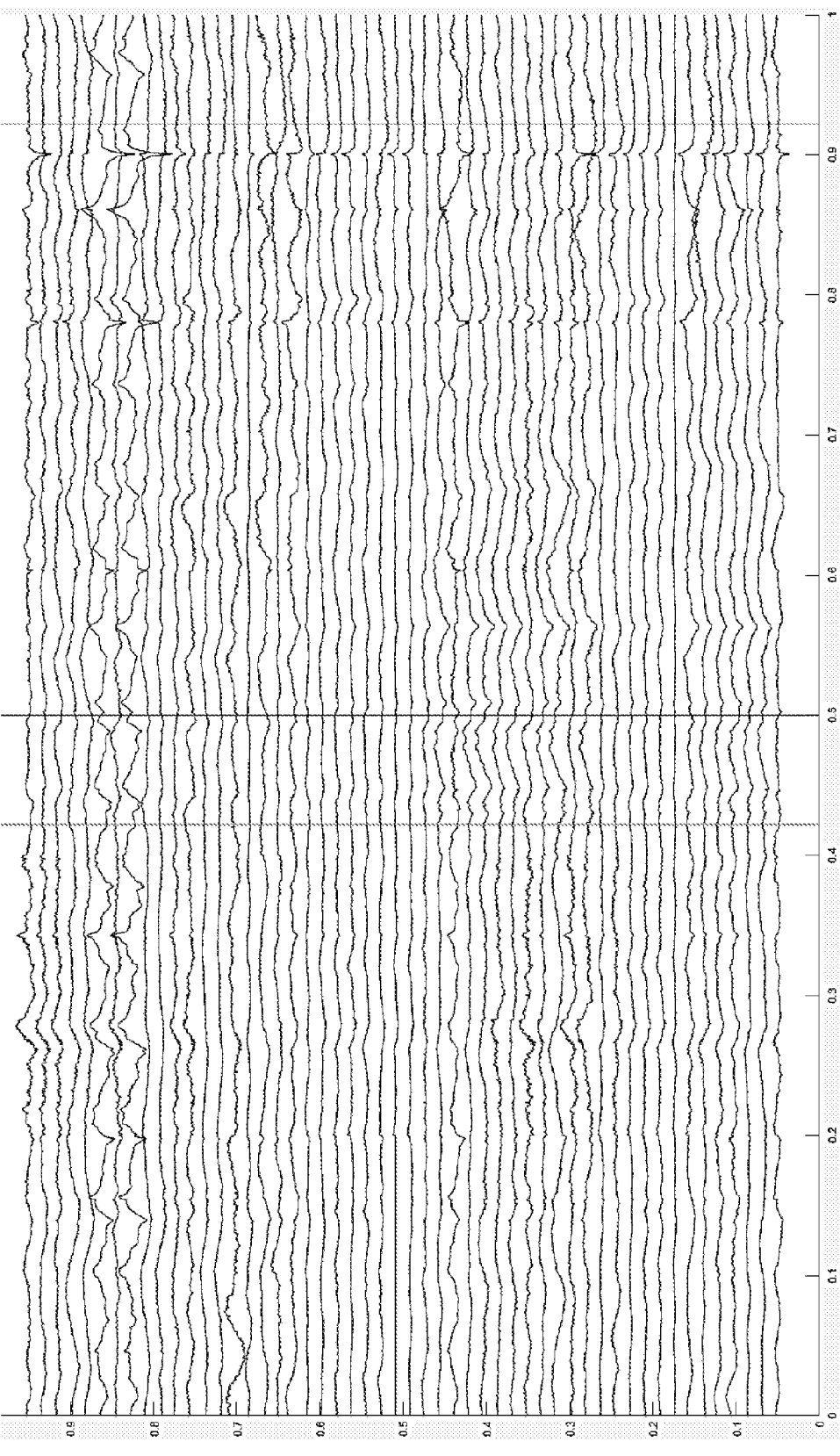
FIGS. 8C and 9C show the projected noise components that were removed from the raw EEG data to produce the cleaned EEG data using an exemplary system of the present disclosure for each of the respective 10-second segments.
Figure 9A:
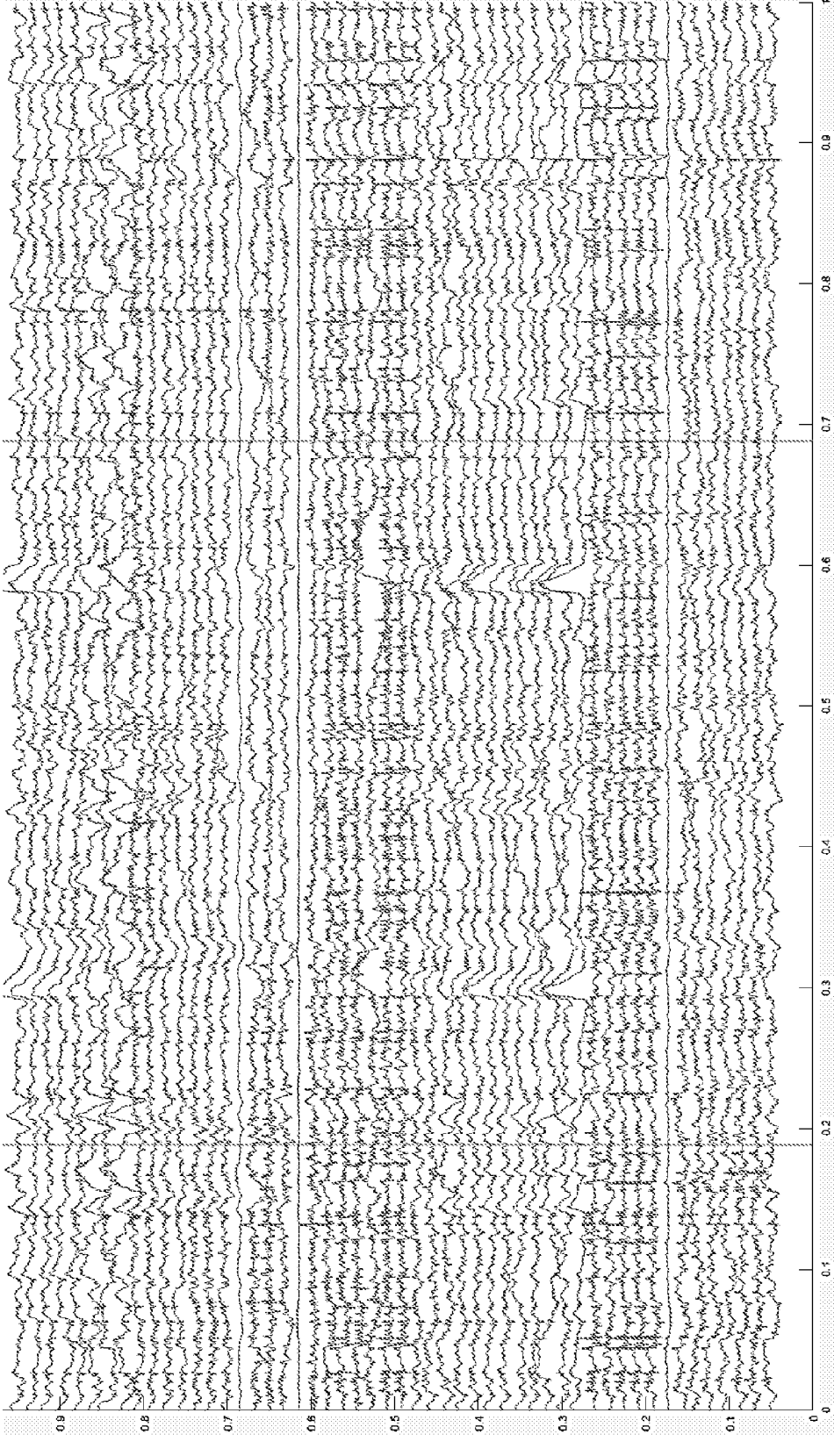
Figure 9B:
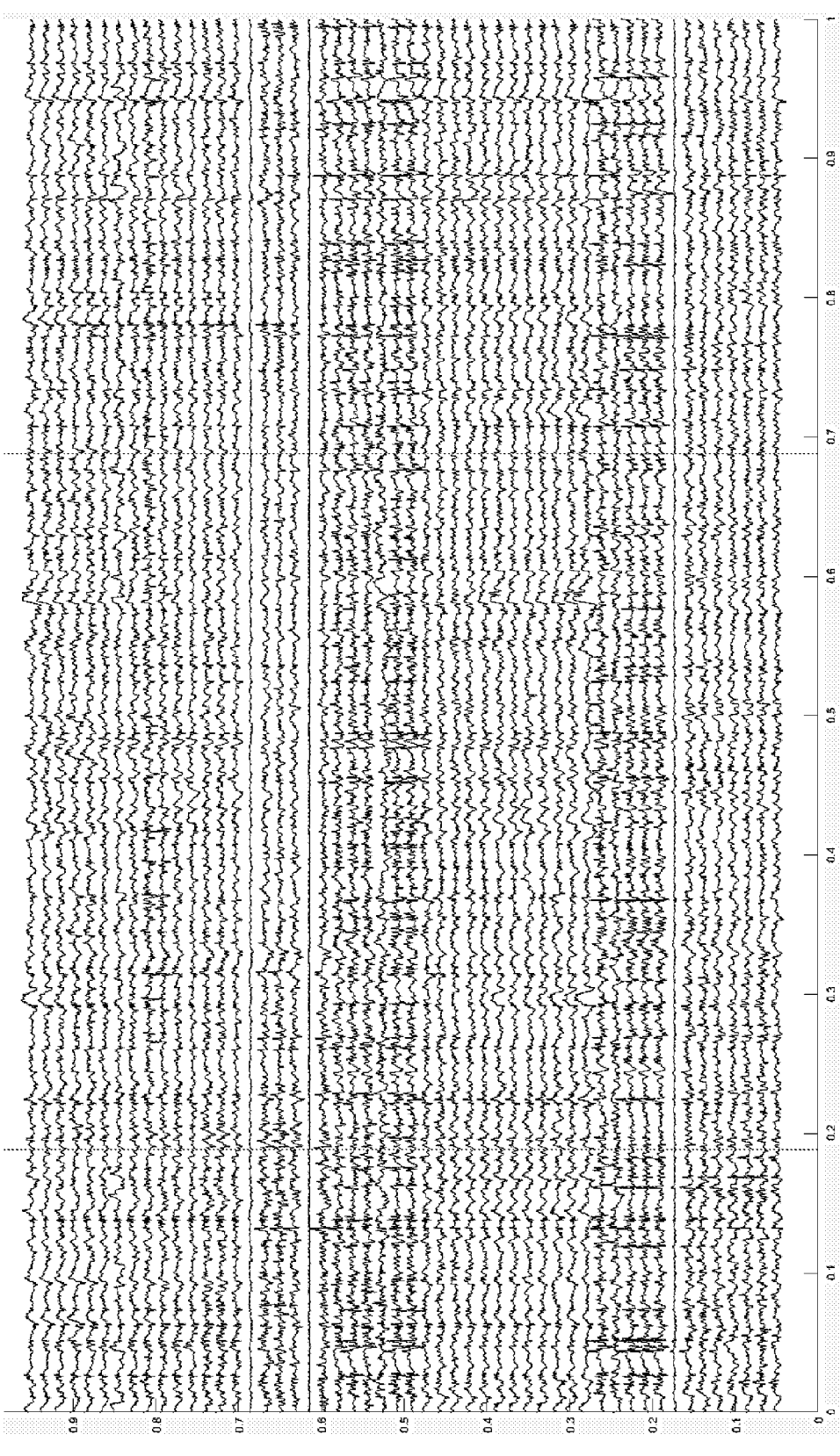
Figure 9C:
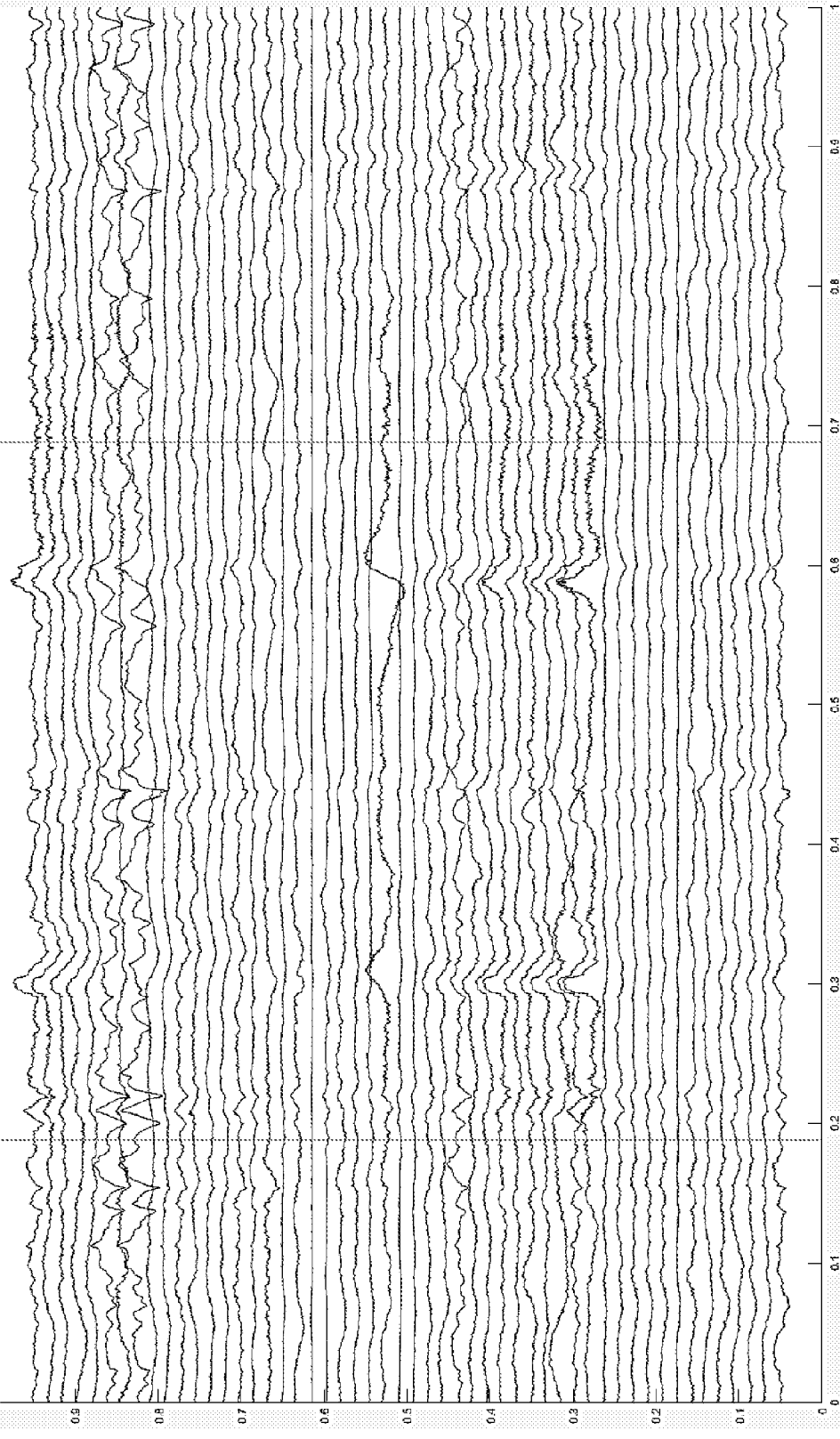

Correspondingly, FIGS. 8A and 9A show the raw EEG data recorded from the EEG electrodes during uneven terrain walking over two different 10-second-long data segments for a subject with particularly bad motion artifacts (before cleaning), and FIGS. 8B and 9B show the cleaned EEG data after the noise components have been removed using an exemplary system of the present disclosure for each of the respective time segments. As such, FIGS. 8C and 9C show the projected noise components that were removed from the raw EEG data (FIGS. 8A and 9A) to produce the cleaned EEG data (FIGS. 8B and 9B) using an exemplary system of the present disclosure.

Figure 10:
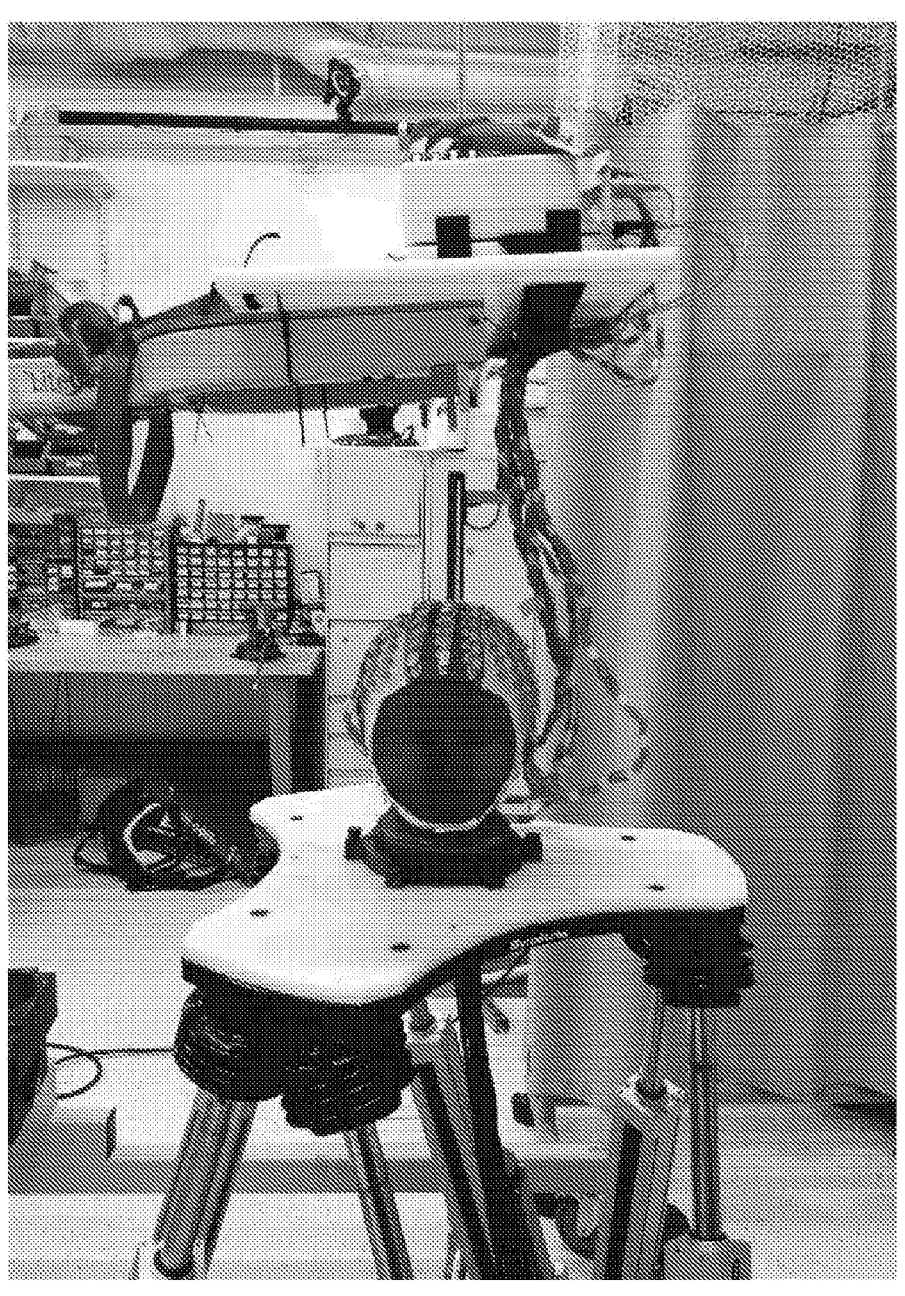
FIG. 10 shows a photograph image of the phantom head and hexapod platform assembly in accordance with various embodiments of the present disclosure.

In additional trials, a phantom head, having EEG electrodes and noise electrodes, was used in place of a human subject. The phantom head was made out of ballistics gelatin and salt to mimic the physical properties as well as the conductivity of a human head. The phantom head was configured with known ground-truth brain sources (via wires in the head with known input signals) and could be moved with a hexapod platform along a trajectory that matched human walking (as well as other trajectories not currently shown such as movement during tennis play). For testing purposes, cables were loosely arranged to induce large motion artifacts (from cable sway), and neck muscle artifacts were inputted into the phantom head to contaminate the EEG channels as well. FIG. 10 shows an image of the phantom head and hexapod platform assembly (also referred to as a "phantom head assembly"). This apparatus/assembly allows for the insertion and subsequent recording of known ground-truth brain signals via antennae placed in the conductive phantom head. It also allows for the purposeful contamination of the brain signals (e.g., with other antennae embedded in the phantom to emit muscle artifacts or by moving the phantom via the hexapod assembly to induce motion artifacts on the EEG signals). Accordingly, noisy brain activity of the phantom head (via the EEG electrodes) and reference noise signals (via the noise electrodes) are recorded and processed using an exemplary cleaning algorithm, in accordance with embodiments of the present disclosure.

Figure 11A:
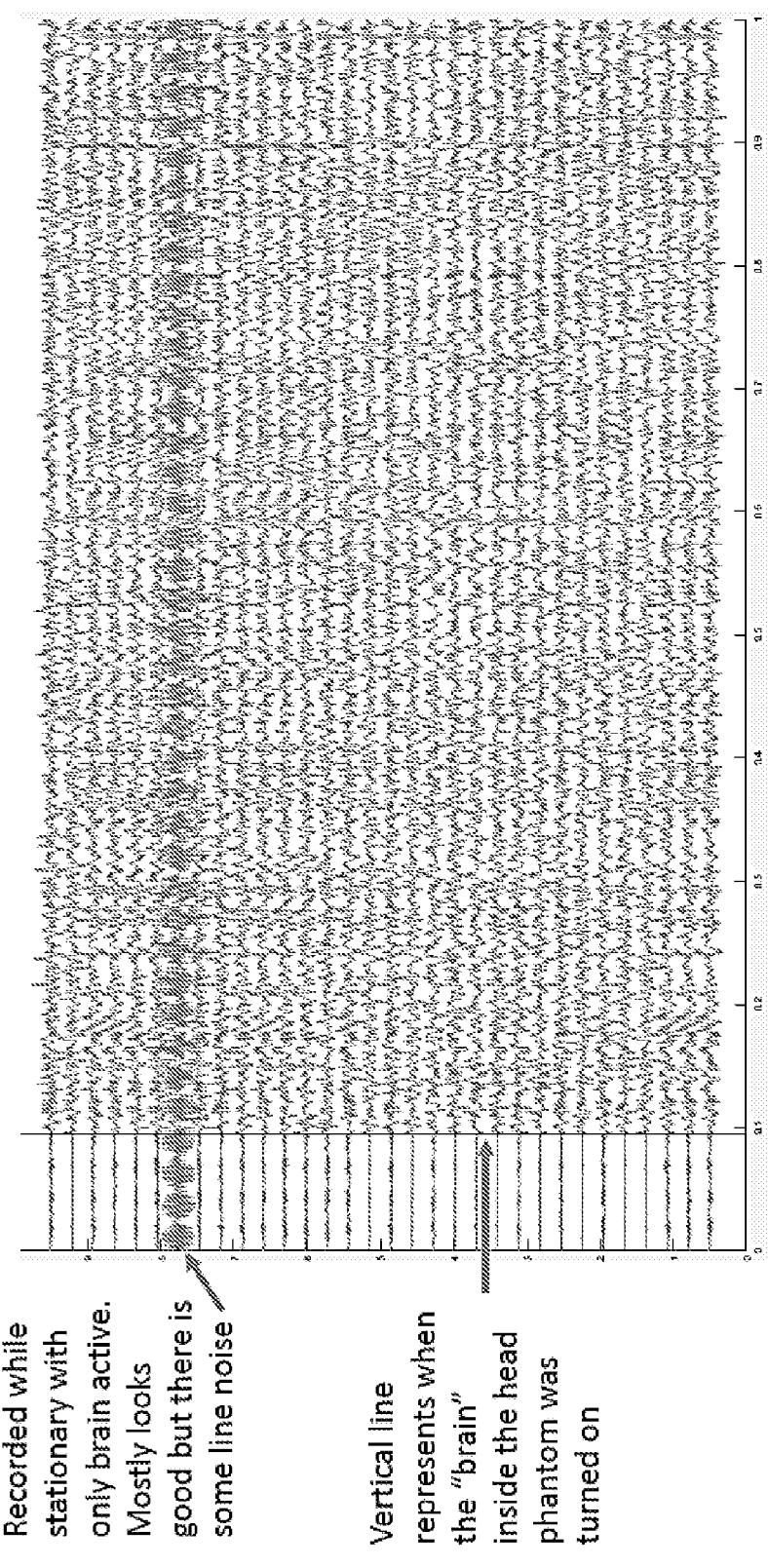
FIG. 11A shows raw EEG data recorded from EEG electrodes over a 10-second segment (before cleaning) for a stationary phantom head assembly of FIG. 10.
Figure 11B:
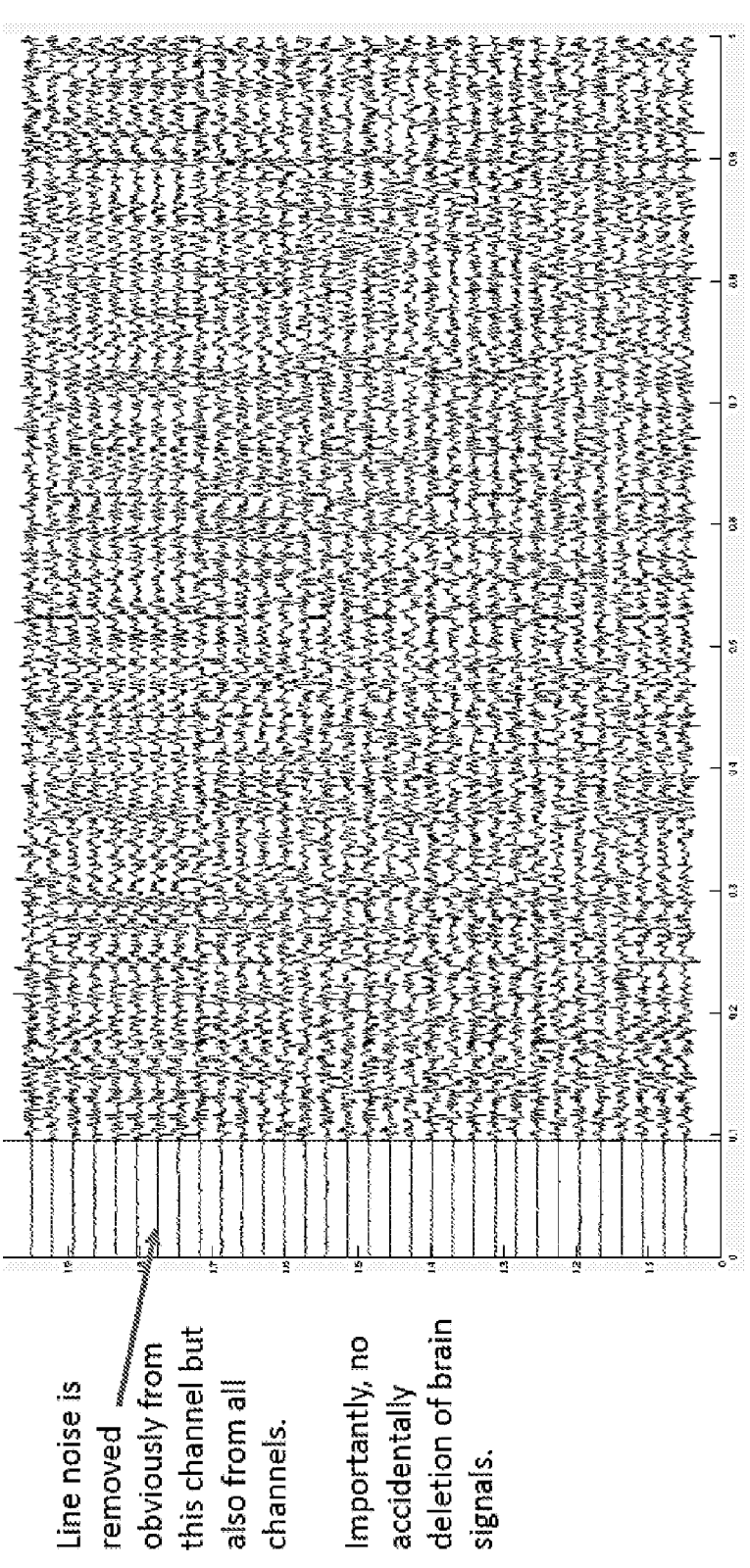
FIG. 11B shows cleaned EEG data after line noise components have been removed using an exemplary system of the present disclosure for the stationary phantom head assembly of FIG. 10.
Figure 11C:
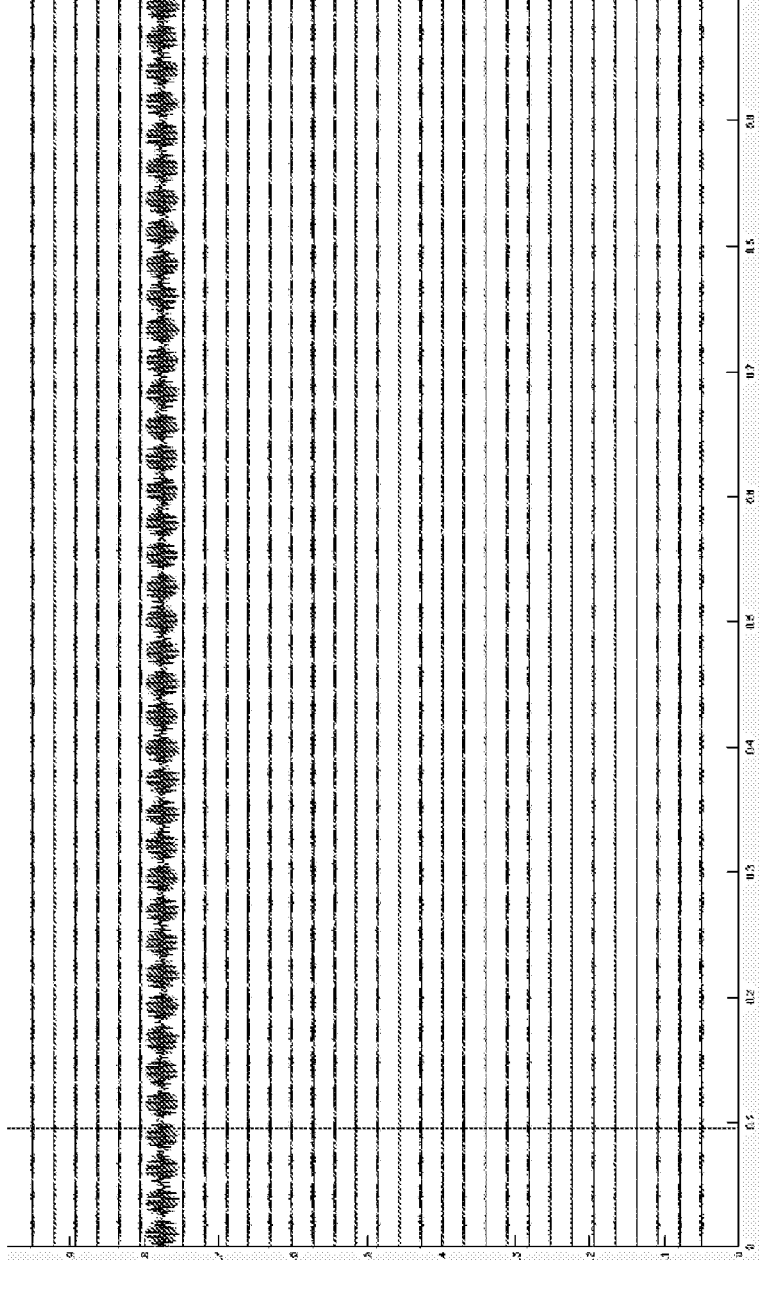
FIG. 11C shows the line noise components that were removed from each of the EEG channels (FIG. 11A) to produce the cleaned EEG data (FIG. 11B) using an exemplary system of the present disclosure.
Figure 11D:
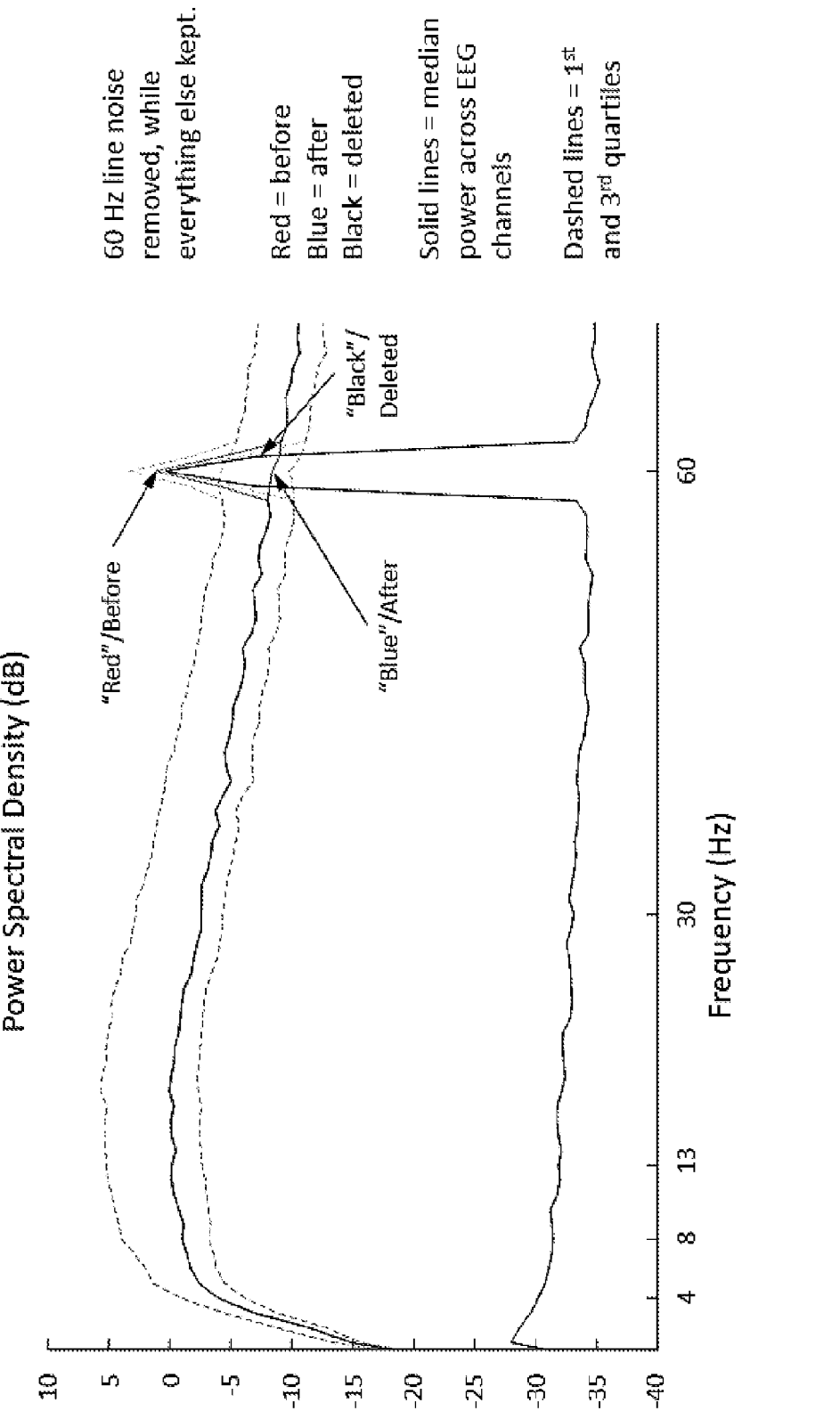
FIG. 11D shows a frequency domain view of the raw phantom EEG data (FIG. 11A), cleaned phantom EEG data (FIG. 11B), and deleted phantom EEG data (FIG. 11C), where solid lines indicate the median power across all channels while dashed lines indicate the first and third quartiles.

Referring now to FIG. 11A, the figure shows the raw EEG data recorded from the EEG electrodes/channels over a 10-second segment (before cleaning) for the phantom head assembly. The vertical line on the plot represents when the "brain" inside the head phantom was turned on. In this scenario, the EEG data was recorded while the phantom head assembly was stationary with only the brain being active to simulate an ideal recording scenario with minimal artifacts (no movement related artifacts or muscle artifacts but still external sources of noise such as those caused by electromagnetic interference from standard 120-Volt electricity running through the walls, termed line noise). While the recorded EEG data appears satisfactory and relatively clean, there is some 60 Hz line noise clearly present. Next, FIG. 11B shows the cleaned EEG data after the line noise components have been removed using an exemplary system of the present disclosure for the phantom head. The line noise is shown to be removed from all of the EEG channels, with no accidental deletion of the brain signals. Correspondingly, FIG. 11C shows the line noise components that were removed from all of the EEG channels (FIG. 11A) to produce the cleaned EEG data (FIG. 11B) using an exemplary system of the present disclosure. Referring now to FIG. 11D, the figure shows a frequency domain view of the raw phantom EEG data, cleaned phantom EEG data, and deleted phantom EEG data, where solid lines indicate the median power across all channels while dashed lines indicate the first and third quartiles. The figure shows that 60 Hz line noise was singularly removed from the EEG data. Importantly, note that, unlike using a notch filter to remove line noise which would delete all 60 Hz activity, there is still power in the 60 Hz range after cleaning with the exemplary system of the present disclosure. This remaining power corresponds to the underlying 60 Hz activity of the ground truth brain signals that were input to the phantom. Thus, the exemplary system deleted 60 Hz line noise without accidentally deleting 60 Hz brain activity.

Figure 12A:
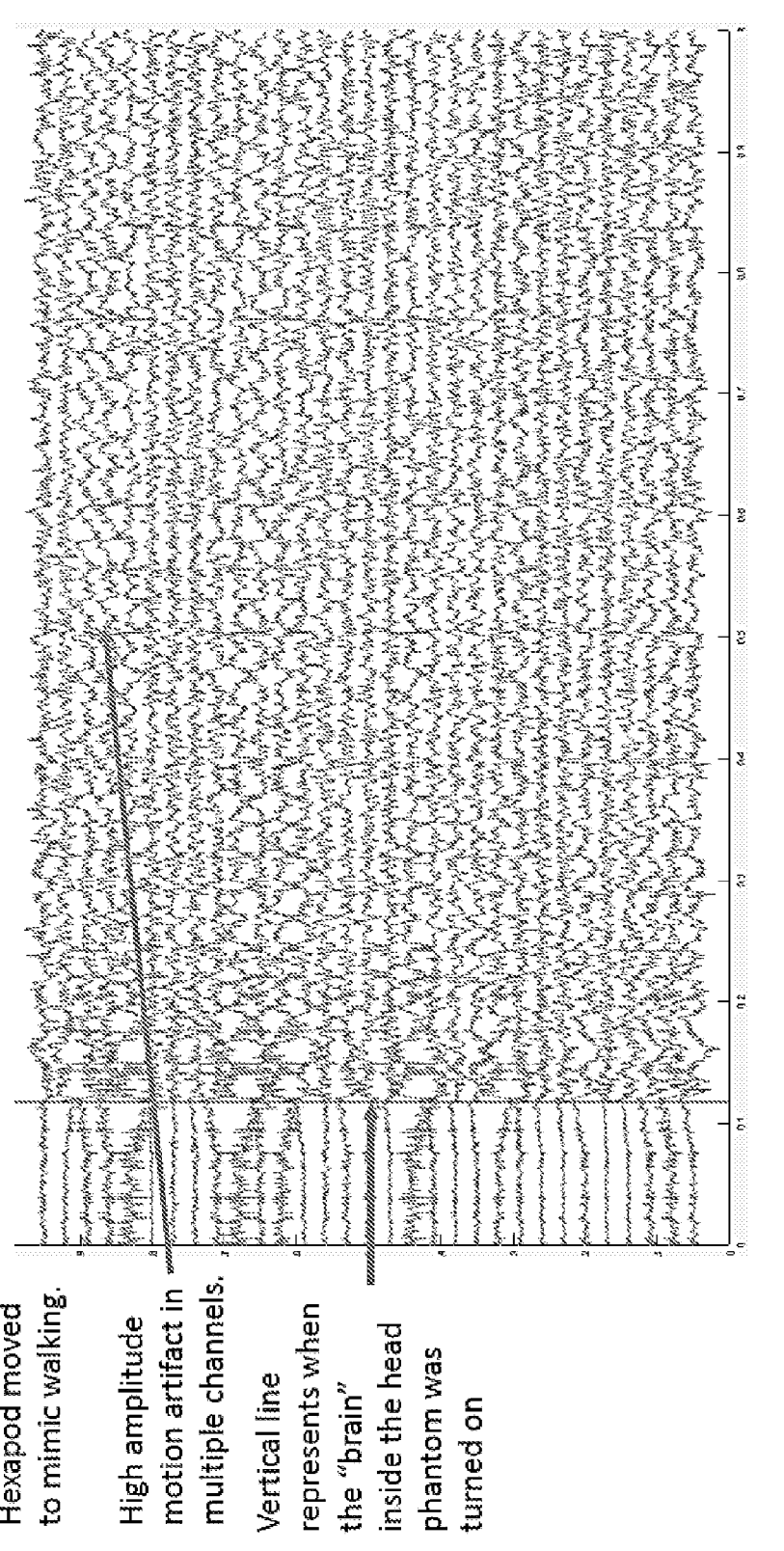
FIG. 12A shows raw EEG data recorded from EEG electrodes/channels over a 10-second segment (before cleaning) for a walking phantom head assembly of FIG. 10.

Next, FIGS. 12A-12D are directed to motion artifact removal using the phantom head assembly. In FIG. 12A, the figure shows the raw EEG data recorded from the EEG electrodes/channels over a 10-second segment (before cleaning) for the phantom head assembly while the phantom head assembly was moved to mimic a walking trajectory, thereby causing cable sway and inducing motion artifacts.

Figure 12B:
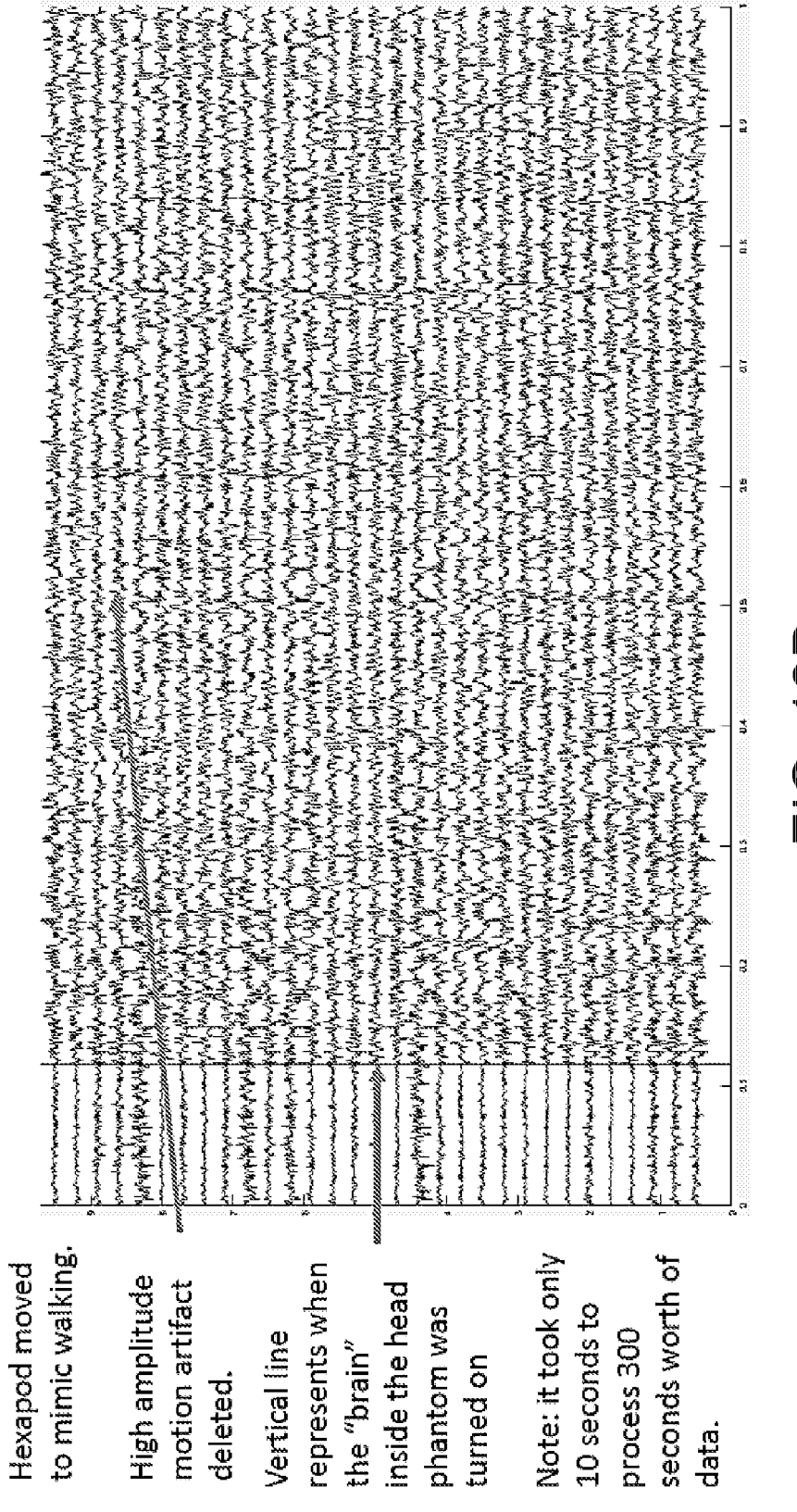
FIG. 12B shows cleaned EEG data after motion artifacts have been removed using an exemplary system of the present disclosure for the walking phantom head assembly of FIG. 10.
Figure 12C:
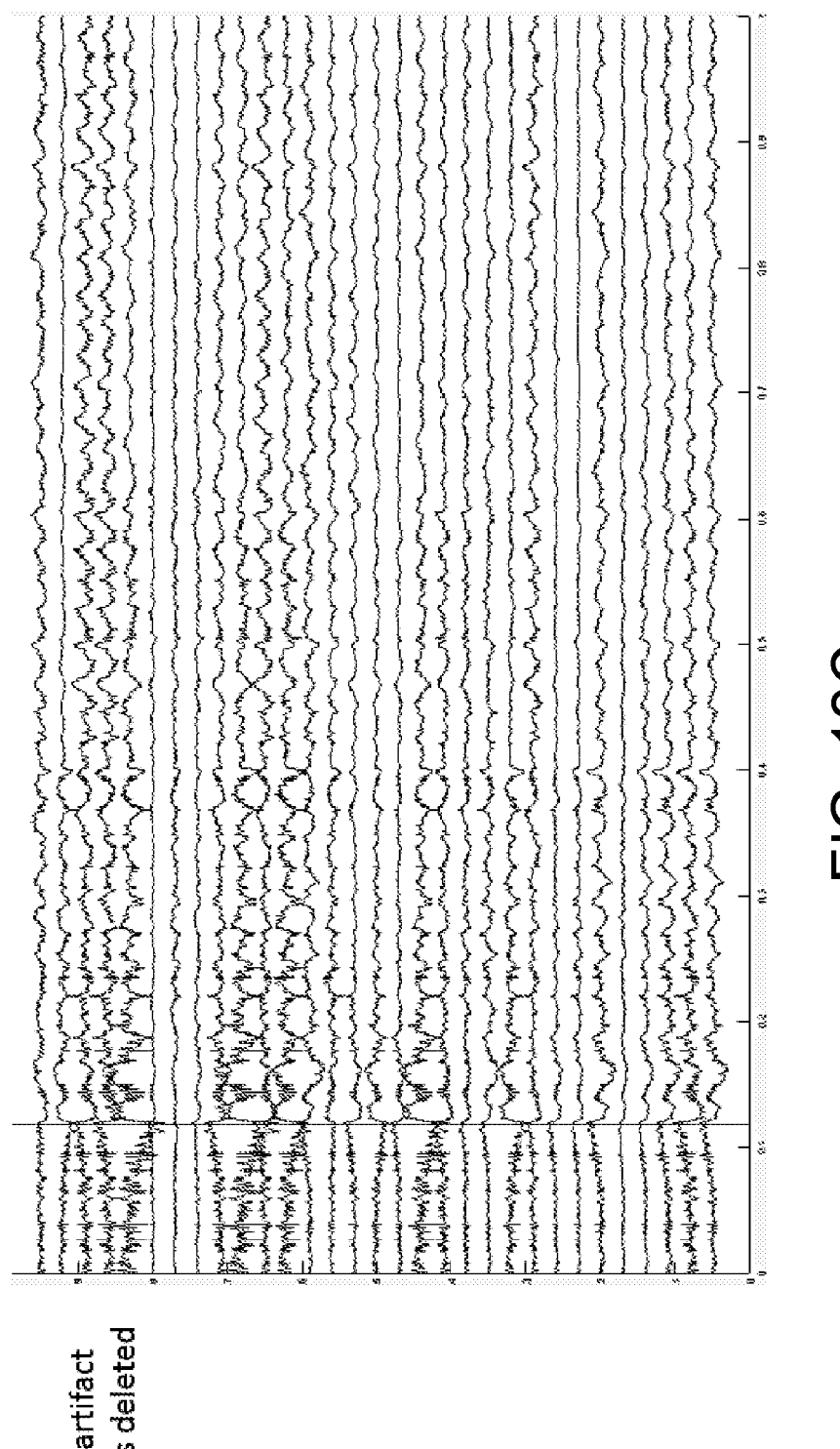
FIG. 12C shows the motion artifacts that were removed from each of the EEG channels (FIG. 12A) to produce the cleaned EEG data (FIG. 12B) using an exemplary system of the present disclosure.
Figure 12D:
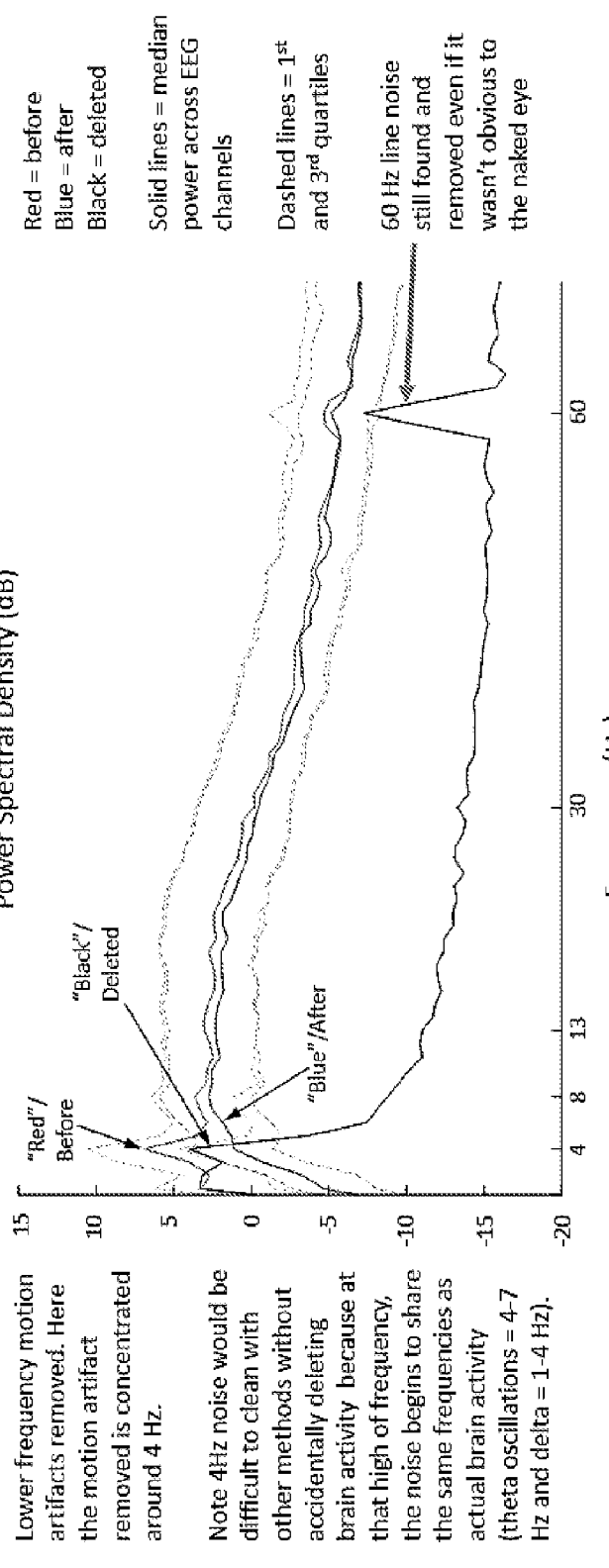
FIG. 12D shows a frequency domain view of the raw phantom EEG data (FIG. 12A), cleaned phantom EEG data (FIG. 12B), and deleted phantom EEG data (FIG. 12C), where solid lines indicate the median power across all channels while dashed lines indicate the first and third quartiles.

The vertical line on the plot represents when the "brain" inside the head phantom was turned on and when the hexapod began to move. Accordingly, the EEG data was recorded while the phantom head assembly was walking with the brain active, thereby producing noisy phantom data (having movement or motion artifacts). The figure shows high-amplitude motion artifacts in multiple channels. FIG. 12B shows the cleaned EEG data after the motion artifacts have been removed using an exemplary system of the present disclosure for the phantom head assembly. The high-amplitude motion artifacts are shown to be removed from all of the EEG channels, with no accidental deletion of the brain signals. It is noted that it only took 10 seconds to process 300 seconds worth of data with a standard personal computer (not a supercomputer). Correspondingly, FIG. 12C shows the noise components (walking motion artifacts, line noise) that were removed from all of the EEG channels (FIG. 12A) to produce the cleaned EEG data (FIG. 12B) using an exemplary system of the present disclosure. Referring now to FIG. 12D, the figure shows a frequency domain view of the raw phantom EEG data, cleaned phantom EEG data, and deleted phantom EEG data, where solid lines indicate the median power across all channels while dashed lines indicate the first and third quartiles. The figure shows that lower frequency motion artifacts (concentrated around 4 Hz) were removed. It is further noted that 4 Hz noise would be difficult to clean with other methods without accidentally deleting brain activity because at that high of frequency, the noise can share the same frequencies as actual brain activity (theta oscillations=4-7 Hz and delta=1-4 Hz). Also, of note, the figure shows that the 60 Hz line noise was simultaneously found and removed via the exemplary system, even if its presence was not as obvious to the naked eye in the previous figures (motion artifacts were large enough that they obscured the presence of line noise on the raw time series).

Figure 13A:
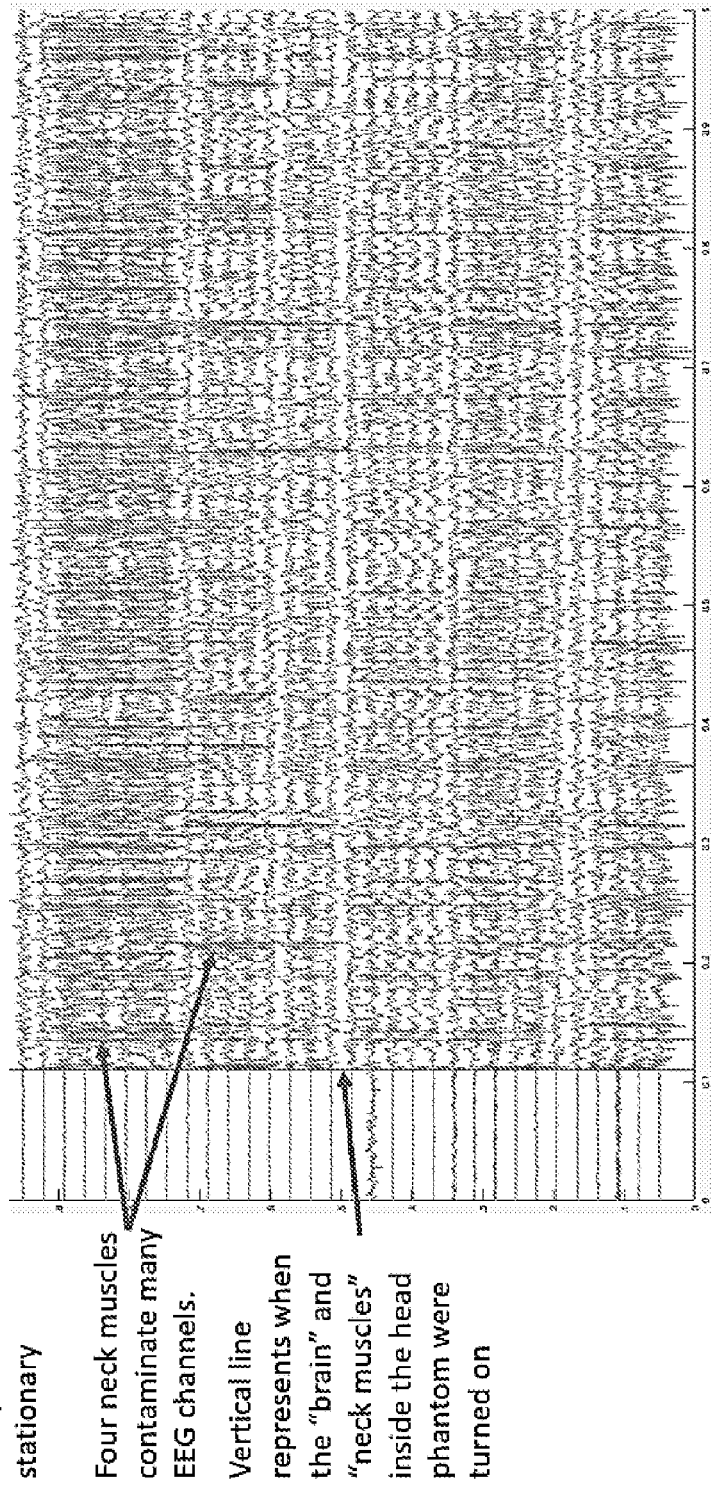
FIG. 13A shows raw EEG data recorded from EEG electrodes/channels over a 10-second segment (before cleaning) for a stationary phantom head assembly of FIG. 10 with neck muscle contamination.
Figure 13B:
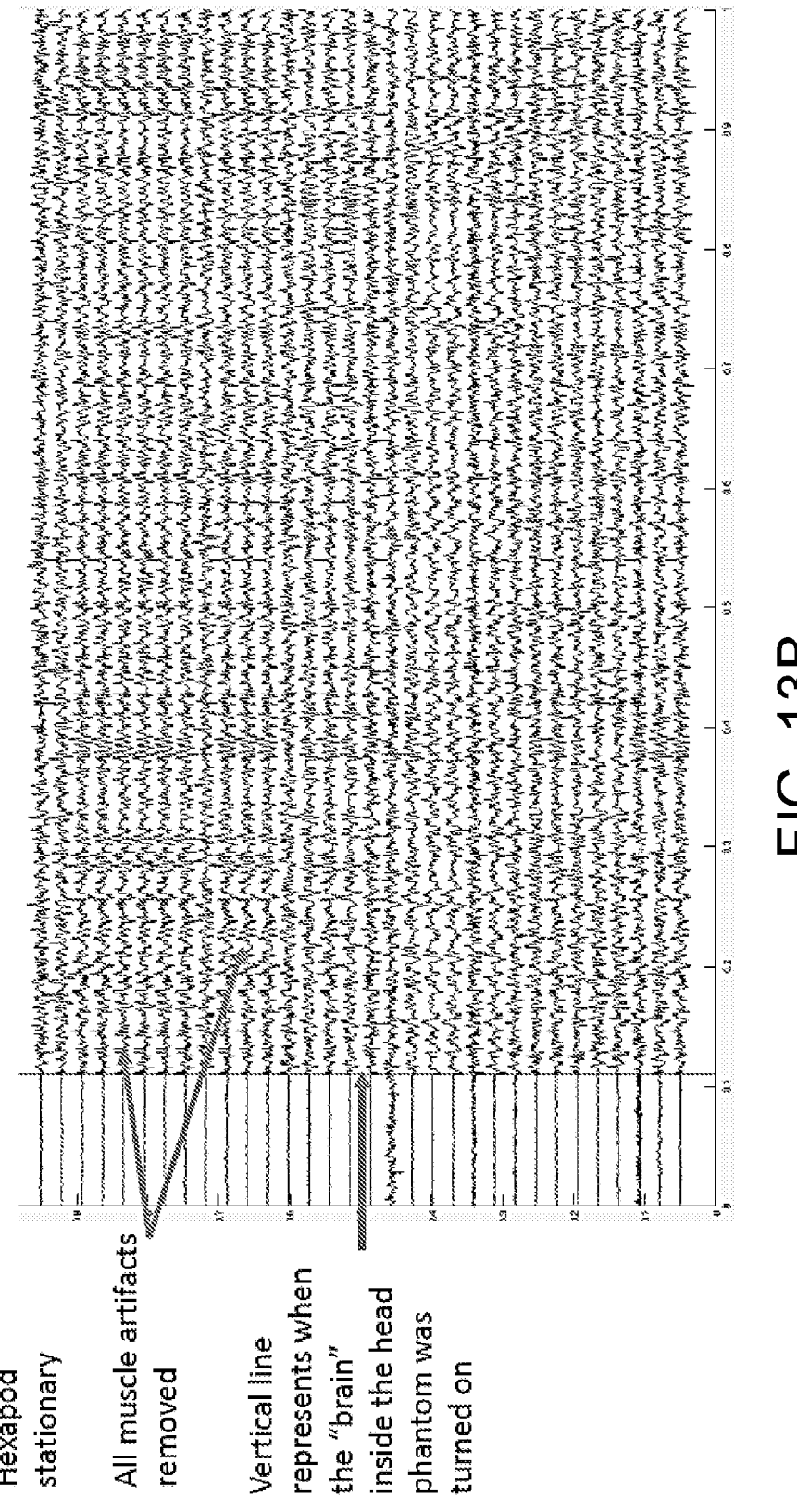
FIG. 13B shows cleaned EEG data after muscle artifacts have been removed using an exemplary system of the present disclosure for the stationary phantom head assembly of FIG. 10 with neck muscle contamination.
Figure 13C:
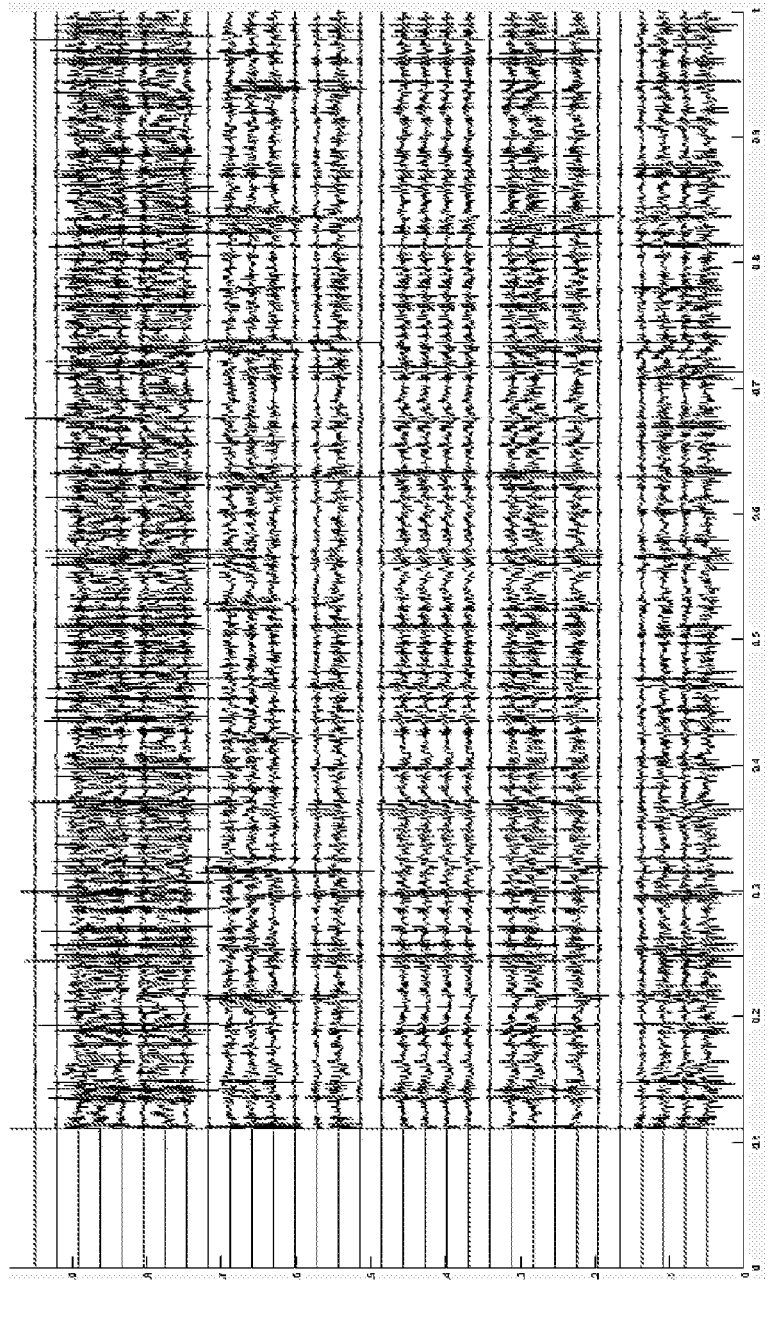
FIG. 13C shows the muscle artifacts that were removed from each of the EEG channels (FIG. 13A) to produce the cleaned EEG data (FIG. 13B) using an exemplary system of the present disclosure.
Figure 13D:
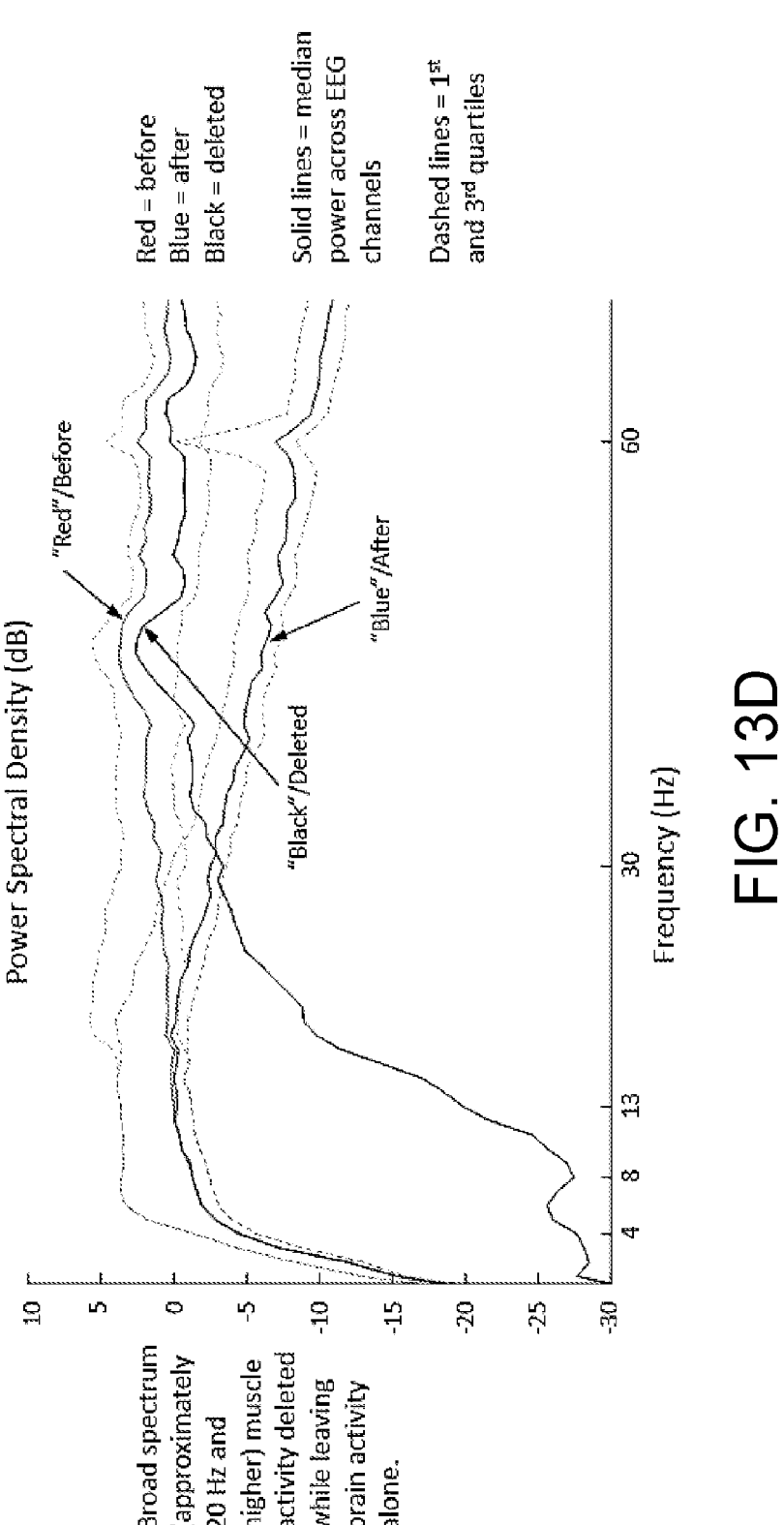
FIG. 13D shows a frequency domain view of the raw phantom EEG data (FIG. 13A), cleaned phantom EEG data (FIG. 13B), and deleted phantom EEG data (FIG. 13C), where solid lines indicate the median power across all channels while dashed lines indicate the first and third quartiles.

Next, FIGS. 13A-13D are directed to neck muscle contamination and removal using the phantom head assembly. In FIG. 13A, the figure shows the raw EEG data recorded from the EEG electrodes/channels over a 10-second segment (before cleaning) for the phantom head assembly while the phantom head assembly was stationary. The vertical line on the plot represents when the "brain" and four "neck muscles" inside the head phantom were turned on. Accordingly, the EEG data was recorded while the phantom head assembly was stationary with only the brain and neck muscles active, thereby producing noisy phantom data (having neck muscle contamination across many EEG channels). During testing, EMG (electromyogram) sensors were placed over the neck of the phantom head as the noise sensors in this case (rather than using dual-layer EEG sensors which are intended to detect motion and line noise artifacts). Accordingly, in various embodiments, any type of noise sensor can be used that is capable of providing a reference signal for the noise that is intended to be removed (e.g., dual-layer EEG sensor, electromyogram, electrooculogram, electrocardiogram, etc.) from a primary data signal (e.g., EEG data signal). FIG. 13B shows the cleaned EEG data after the muscle artifacts have been removed using an exemplary system of the present disclosure for the phantom head assembly. The muscle artifacts are shown to be removed from all of the EEG channels, with no accidental deletion of the brain signals. Correspondingly, FIG. 13C shows the noise components (muscle artifacts) that were removed from all of the EEG channels (FIG. 13A) to produce the cleaned EEG data (FIG. 13B) using an exemplary system of the present disclosure. Referring now to FIG. 13D, the figure shows a frequency domain view of the raw phantom EEG data, cleaned phantom EEG data, and deleted phantom EEG data, where solid lines indicate the median power across all channels while dashed lines indicate the first and third quartiles. The figure shows that broad spectrum muscle activity (approximately 20 Hz and higher) was removed from the raw EEG data while leaving brain activity alone. Additionally, while the motion artifact and neck muscle artifact removal are shown separately for visual clarity in the foregoing figures, multiple types of artifacts can be cleaned simultaneously in accordance with embodiments of the present disclosure as long as appropriate noise sensors are available for each type of noise the user wishes to remove.

As a final demonstration of the potential impact of the invention described in the present disclosure, a pseudo real-time experiment was performed. Specifically, the inventor took data that was previously recorded (offline data) and adjusted the implementation of the exemplary cleaning algorithm so that it simulated a real-time cleaning scenario. Specifically, although the cleaning was performed offline, the exemplary algorithm was limited to only having access to the immediately preceding 2 seconds of data at any given time (i.e., it could not see into the future nor see far into the past). Data were cleaned chunk by chunk (via a for loop) on the offline data (30 Hz refresh rate, 33 ms chunks to be cleaned at a time, 2-second history of data for CCA to identify noise components). The exemplary cleaning algorithm was verified to run faster than needed for real-time (e.g., 100 seconds worth of data can be cleaned in less than 100 total seconds in the pseudo real-time setup).

Figure 14:
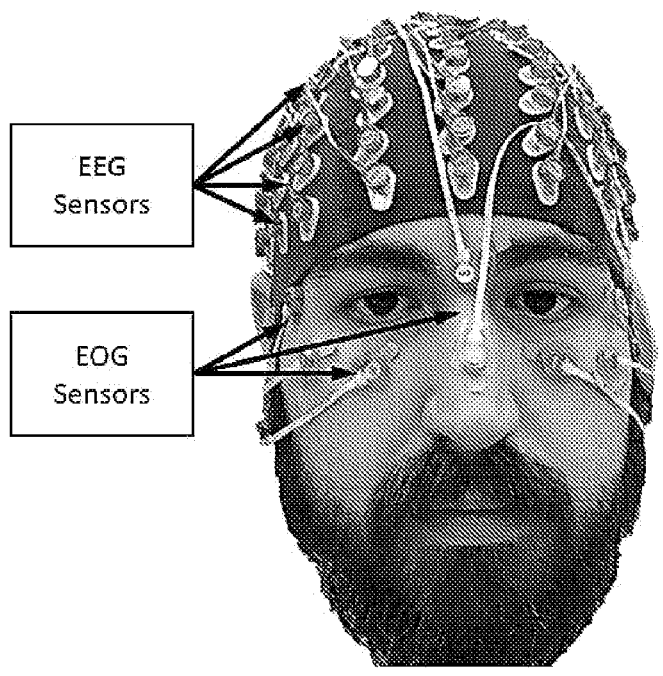
FIG. 14 depicts a photograph image of 8 electrooculogram (EOG) sensors that were placed on the face around the eyes of a subject for exemplary removal of eye artifacts from EEG data.
Figure 15:
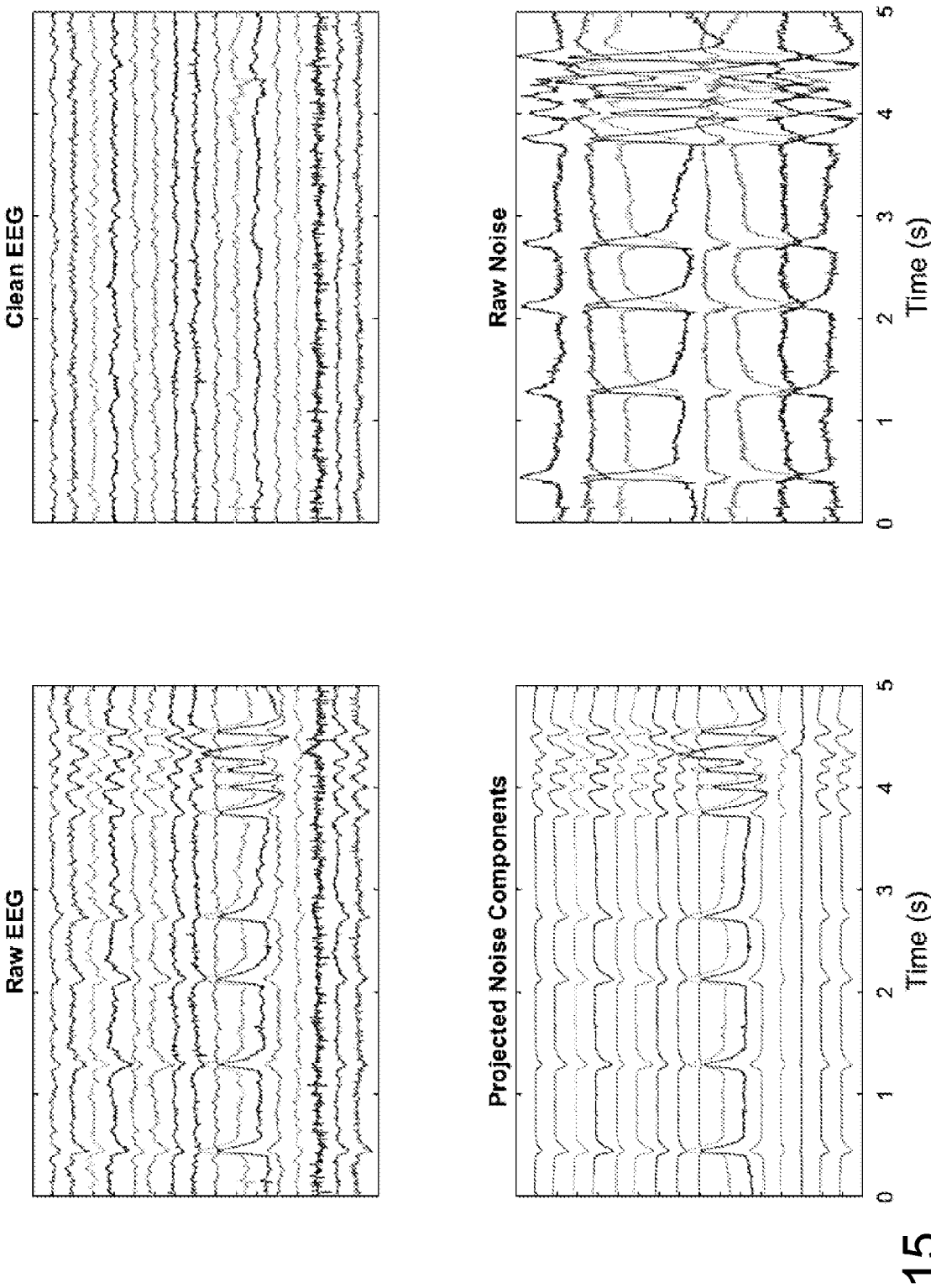
FIG. 15 depicts the results from an exemplary pseudo real-time implementation of the methods described in the present disclosure to remove eye artifacts using EOG sensors. The top left image depicts the raw EEG data while the bottom right image depicts the raw noise sensors.

First the exemplary pseudo real-time algorithm was implemented to remove eye artifacts from EEG data. For real-time applications, even in the absence of motion artifacts, eye artifacts can significantly hinder their performance since eye blinks are much larger than electrical brain activity at the scalp (e.g., 100-150 uV for eye artifacts versus 20 uV for brain activity). FIG. 14 depicts a human subject wearing an EEG cap along with 8 EOG sensors around the eyes (to act as noise sensors for the exemplary algorithm). Here, the experiment was designed to remove eye blink artifacts, but the setup can also be used to remove eye saccade artifacts (eye movement). FIG. 15 demonstrates the results of the exemplary pseudo real-time implementation where eye blink artifacts are removed from the EEG channels without deleting brain activity. The top left image depicts the raw EEG data while the bottom right image depicts the raw noise sensors (here EOG sensors). CCA was used to find latent noise components common to both sets of signals. Those noise components were then scaled appropriately to match the raw EEG data (i.e., their projections calculated), as is shown in the bottom left image. Finally, the projected noise was deleted from the raw EEG data, and the clean EEG data was obtained, as is depicted in the upper right image. Note, only a subset of EEG sensors are shown for visual clarity (approximately $\frac{1}{8}^{th}$ of the total sensors) but all 8 noise (EOG) sensors are shown. Further, although the raw noise sensors already moderately resemble the artifacts that appear on the EEG data, their individual recordings are not perfect, and the projected noise components that were removed with the exemplary algorithm were a more accurate representation of the eye artifacts than the raw noise sensors by themselves. That is, eye artifacts are better removed by using CCA on multi-channel EEG and reference noise data than what could be achieved by using individual noise channels alone. Note that no low-pass filtering was applied to create the smooth looking noise components in FIG. 15; the smoothness (improved compared to the raw noise sensors alone) is simply a result of CCA being able to find latent sources of noise hidden amongst the EEG and noise sensors.

Figure 16:
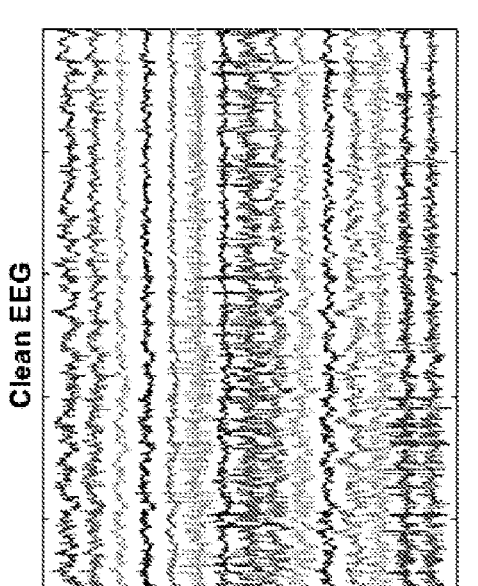
FIG. 16 depicts the results from an exemplary pseudo real-time implementation of the methods described in the present disclosure to remove motion artifacts using dual-layer EEG sensors. The top left image depicts the raw EEG data while the bottom right image depicts the raw noise sensors.
Figure 16:
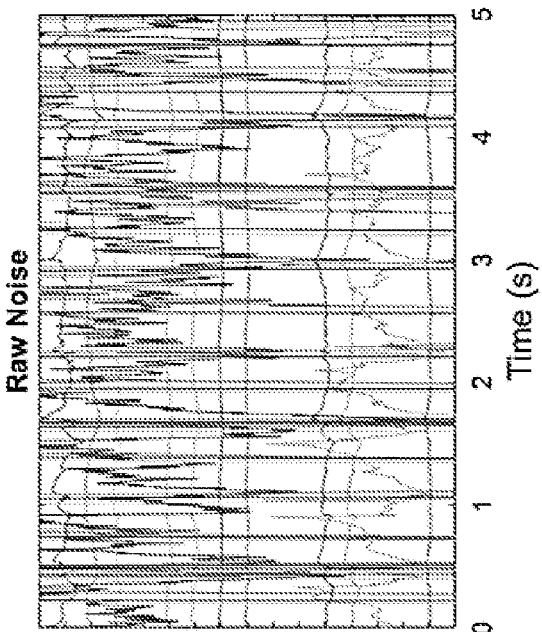
Figure 16:
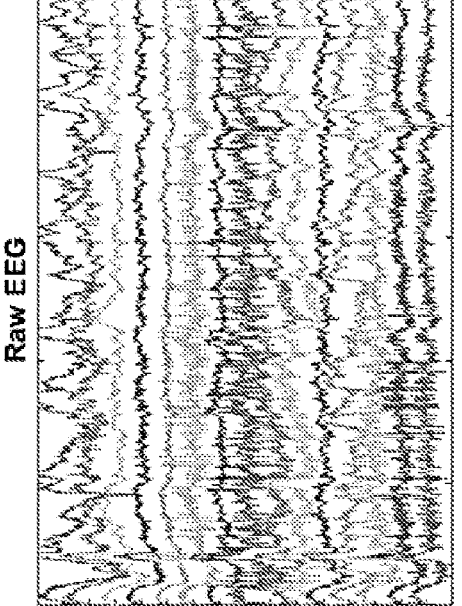
Figure 16:
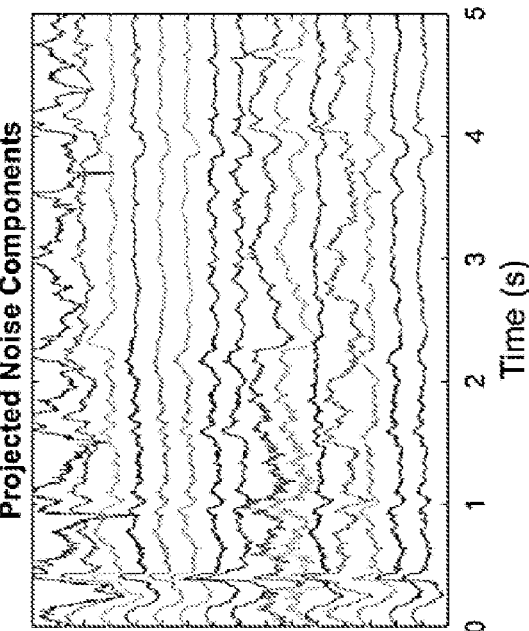

Next, the exemplary pseudo real-time algorithm was implemented to remove motion artifacts from mobile EEG data. For many real-time applications, motion artifacts are a significant hindrance. For example, brain-controlled exo-skeletons to help individuals with paralysis regain move-ment could greatly benefit from the real-time removal of motion artifacts from EEG. Similarly, brain computer inter-faces for neuro-rehabilitation applications could be acceler-ated to the market by utilizing systems/methods of the presently disclosure, as would other commercial applica-tions outside of the medical realm such as brain computer interfaces for virtual reality games where the user's thoughts must be read while the user is actively moving around in physical space. To demonstrate the ability to remove motion artifacts in real-time, data from uneven walking experiments in human subjects (previously discussed) was run in pseudo real-time. FIG. 16 demonstrates the results of the exemplary pseudo real-time implementation where motion artifacts are removed from EEG data using a dual-layer setup for the noise sensors. The top left image depicts the raw EEG data while the bottom right image depicts the raw noise sensors (here dual-layer EEG sensors). CCA was used to find latent noise components common to both sets of signals. Those noise components were then scaled appropriately to match the raw EEG data (i.e., their projections calculated), as is shown in the bottom left image. Finally, the projected noise was deleted from the raw EEG data, and the clean EEG data was obtained, as is depicted in the upper right image. Note only a subset of the EEG and noise sensors are shown for visual clarity (approximately ⅛$^{th}$ of the total sensors). Note that in FIG. 16, there is a perfect one-to-one match between the noise sensors and the EEG sensors (unlike the real-time eye artifact removal setup where there were only 8 EOG sensors and 100+ EEG sensors, here all 100+ EEG sensors have a corresponding noise electrode paired to them). Matching (paired) channels from the dual-layer setup are denoted by their vertical placement and the color of their time series (e.g., the topmost (blue) time series in the "Raw EEG" plot comes from an EEG electrode that was physically paired with the noise electrode shown in the topmost (blue) time series in the "Raw Noise" plot). Note that, the artifacts recorded by the raw noise sensors in FIG. 16 do not so evidently appear to be directly related to the artifacts appear-ing on the raw EEG sensors (cf. the raw EOG noise sensors more obviously resembling the eye artifacts on the raw EEG of FIG. 15). This demonstrates, for example, why the method by Rasheed et al. would have difficulty cleaning the EEG data in FIG. 16 using only a single noise reference to clean each EEG channel. Meanwhile, the exemplary algo-rithm used CCA to exploit the information contained within the entire set of EEG sensors and noise sensors (all channels considered simultaneously) to identify latent noise compo-nents in common to all EEG channels which yields greater cleaning performance.

After completion of experimental trials, visual results of an implementation of the signal cleaning algorithm have been shown to be significant. In multiple trials, an exem-plary system was tested on human data and also validated with a phantom head, where the ground truth signals were known so that the results could be quantified. The cleaning algorithm, as performed by the exemplary system, was able to remove a plurality of artifacts from noisy EEG channels. For example, the system was able to remove motion artifacts caused from EEG cables swaying through the air and the EEG electrodes moving on the scalp as people moved around (e.g., walking over uneven terrain). The system was also able to remove line noise (50 or 60 Hz) contamination that exists even in traditional (stationary) EEG data caused by electricity running through the walls. Additionally, muscle artifacts were able to be removed via the cleaning algorithm of the exemplary system by using EMG electrodes as reference noise sensors alongside traditional EEG sen-sors. Finally, eye artifacts were able to be removed via the cleaning algorithm of the exemplary system by using EOG sensors as reference noise recordings. Accordingly, it is contemplated that other types of artifacts may also be removed via systems and methods of the present disclosure, for example, artifacts that occur while recording EEG inside a magnetic resonance imaging scanner, artifacts from a transcranial magnetic stimulator, or artifacts from other electromagnetic devices that may be nearby a subject. Cor-respondingly, systems and methods of the present disclosure are not limited to being applied to only noisy EEG signals and can be applied in order to clean other types of noisy signals in general (e.g., to remove motion artifacts from a EMG signals). Along these lines, it was demonstrated that an exemplary implementation of methods of the present dis-closure could be minimally modified to be able to remove artifacts in real-time. To accomplish this, the exemplary algorithm was implemented with a moving 2-second win-dow (CCA and noise projections were calculated multiple times over many small time-windows rather than one large window of data). Alternatively, future implementations of the methods of the present disclosure could attempt to recursively calculate the CCA components and/or projec-tions during real-time. That is, rather than only using the information available in the most recent small window of time, a recursive algorithm could contain the past history of data points and progressively update the calculations at each iteration without being computationally burdensome. Recur-sive CCA algorithms exist in literature and fit into the methods described in the present disclosure but have not yet been specifically implemented to verify their potential impact. Similarly, other variations on CCA exist, for example, to improve its robustness to outlier sample points (regularization) or to extend it from a linear solution to a nonlinear one (kernelization). However, these variations on CCA may increase the computational cost and prevent real-time implementation; thus, their specific performance has not yet been tested but fits within the scope of the methods of the present disclosure. Another slight variation on the implementation could include using an external calibration set (e.g., previously recorded data from the current subject or from one or more other subjects). This could be done to save computational time by reducing the number of times CCA must be called (useful for real-time applications), and it could also be used to find noise com-ponents that are generalizable across multiple subjects.

Figure 17:
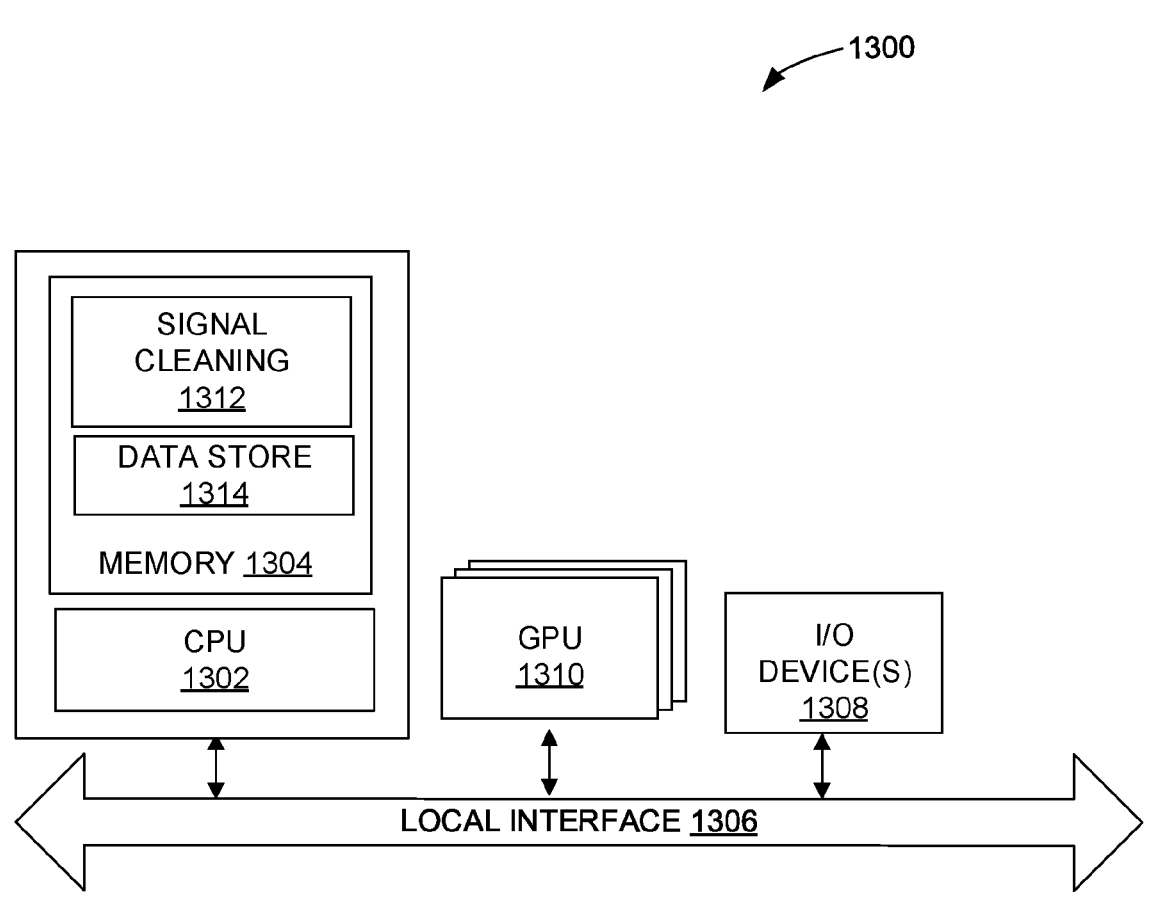
FIG. 17 depicts a schematic block diagram of a computing device that can be used to implement various embodiments of the present disclosure.

FIG. 17 depicts a schematic block diagram of a computing device 1300 that can be used to implement various embodi-ments of the present disclosure. An exemplary computing device 1300 includes at least one processor circuit, for example, having a processor 1302 and a memory 1304, both of which are coupled to a local interface 1306, and one or more input and output (I/O) devices 1308. The local inter-face 1306 may comprise, for example, a data bus with an accompanying address/control bus or other bus structure as can be appreciated. The CPU can perform various operations including any of the various operations described herein.

Stored in the memory 1304 are both data and several components that are executable by the processor 1302. In particular, stored in the memory 1304 and executable by the processor 1302 is a signal cleaning routine 1312 in accordance with embodiments of the present disclosure. Also stored in the memory 1304 may be a data store 1314 and other data. The data store 1314 can include data signal recordings, and potentially other data. In addition, an operating system may be stored in the memory 1304 and executable by the processor 1302. The I/O devices 1308 may include input devices, for example but not limited to, a keyboard, touchscreen, mouse, recording devices, and/or sensors, etc. Furthermore, the I/O devices 1308 may also include output devices, for example but not limited to, a display, speaker, earbuds, audio output port, a printer, etc.

Certain embodiments of the present disclosure can be implemented in hardware, software, firmware, or a combination thereof. If implemented in software, signal cleaning logic or functionality, in accordance with embodiments of the present disclosure, are implemented in software or firmware that is stored in a memory and that is executed by a suitable instruction execution system. If implemented in hardware, the signal cleaning logic or functionality can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. All such modifications and variations are intended to be included herein within the scope of this disclosure.

Therefore, at least the following is claimed:

1. A method comprising:

positioning a plurality of dual-layer sensors on a head of a subject, wherein each individual dual-layer sensor has an electroencephalography (EEG) electrode and a noise electrode, wherein the EEG electrodes for the plurality of dual-layer sensors are positioned to face towards the head of the subject and the noise electrodes for the plurality of dual-layer sensors are positioned to face away from the head of the subject, wherein the EEG electrodes of the plurality of dual-layer sensors each record a data signal across a plurality of EEG channels and the noise electrodes of the plurality of dual-layer sensors each record a reference signal across a plurality of noise channels;

obtaining, from the EEG electrodes by at least one computing device, the data signals across the plurality of EEG channels, wherein the data signals represent brain activity across the plurality of EEG channels, wherein the data signals have artifacts across one or more of the plurality of EEG channels;

obtaining, from the noise electrodes by the at least one computing device, the reference signals representing noise activity across the plurality of noise channels;

analyzing, by the at least one computing device, the data signals with the reference signals to identify noise components that exist within the data signals with the reference signals;

scaling, by the at least one computing device, the noise components to project upon the data signal across the plurality of EEG channels; and cleaning, by the at least one computing device, the data signals by subtracting the scaled noise components from the data signals across each of the plurality of EEG channels.

2. The method of claim 1, wherein the noise components are identified using Canonical Correlation Analysis (CCA).

3. The method of claim 1, wherein the noise electrodes comprise electromyogram (EMG) sensors.

4. The method of claim 1, wherein the noise electrodes comprise electrooculogram (EOG) sensors.

5. The method of claim 1, further comprising determining an optimal scaling factor that explains how each noise component projects onto each of the plurality of EEG channels, wherein the noise components are scaled using the optimal scaling factor.

6. The method of claim 1, wherein after cleaning the data signals, noise sources that overlap with data of interest are deleted without deleting the data of interest.

7. The method of claim 1, wherein the artifacts comprise at least one of motion artifacts, line noise, muscle artifacts, or eye artifacts.

8. The method of claim 1, wherein the scaling of the noise components to project upon the data signals across the plurality of EEG channels is performed using a pseudoinverse solution to solve for noise projections.

9. The method of claim 1, wherein the scaling of the noise components to project upon the data signals across the plurality of EEG channels is performed using a least squares solution to solve for noise projections.

10. A system comprising:

a plurality of dual-layer sensors, wherein each individual dual-layer sensor has an electroencephalography (EEG) electrode and a noise electrode, wherein the EEG electrodes of the plurality of dual-layer sensors are configured to face towards a head of a subject and noise the electrodes for the plurality of dual-layer sensors are configured to face away from the head of the subject;

wherein the EEG electrodes for the plurality of dual-layer sensors are each configured to record a data signal representing brain activity of the subject across a plurality of EEG channels;

wherein noise the electrodes for the plurality of dual-layer sensors are each configured to record a reference signal representing noise activity across a plurality of noise channels; and a computing device that stores a signal cleaning program including computer-executable instructions configured to perform operations comprising:

obtaining recorded data signals representing the brain activity across the plurality of EEG channels, wherein the recorded data signals have artifacts across one or more of the plurality of EEG channels;

obtaining recorded reference signals representing the noise activity across the plurality of noise channels;

analyzing the recorded data signals with the recorded reference signals to identify noise components that exist within the recorded data signals with the recorded reference signals;

scaling the noise components to project upon the recorded data signal across the plurality of EEG channels; and cleaning the recorded data signals by subtracting the scaled noise components from the recorded data signals across each of the plurality of EEG channels.

11. The system of claim 10, wherein the noise components are identified using Canonical Correlation Analysis (CCA).

12. The system of claim 10, wherein the operations further comprise determining an optimal scaling factor that explains how each noise component projects onto each of the plurality of EEG channels, wherein the noise components are scaled using the optimal scaling factor.

13. The system of claim 10, wherein the artifacts comprise motion artifacts.

14. The system of claim 10, wherein the artifacts comprise line noise.

15. The system of claim 10, wherein the artifacts comprise muscle artifacts.

16. The system of claim 10, wherein the artifacts comprise eye artifacts.

17. The system of claim 10, wherein the noise electrodes comprise electromyogram (EMG) sensors.

18. The system of claim 10, wherein the noise electrodes comprise electrooculogram (EOG) sensors.

19. The system of claim 10, wherein the scaling of the noise components to project upon the data signals across the plurality of EEG channels is performed using a pseudoinverse solution to solve for noise projections.

20. The system of claim 10, wherein the scaling of the noise components to project upon the data signals across the plurality of EEG channels is performed using a least squares solution to solve for noise projections.

* * * * *